United States Patent
DiPoto et al.

(10) Patent No.: US 8,939,977 B2
(45) Date of Patent: Jan. 27, 2015

(54) SYSTEMS AND METHODS FOR SEPARATING BONE FIXATION DEVICES FROM INTRODUCER

(71) Applicant: IlluminOss Medical, Inc., East Providence, RI (US)

(72) Inventors: Gene P. DiPoto, Upton, MA (US); Jeffrey P. Brousseau, Barrington, MA (US); Anthony W. O'Leary, Walpole, MA (US); Chi Y. Wong, Canton, MA (US); Robert A. Rabiner, Tiverton, RI (US)

(73) Assignee: IlluminOss Medical, Inc., East Providence, RI (US)

( * ) Notice: Subject to any disclaimer, the term of this patent is extended or adjusted under 35 U.S.C. 154(b) by 0 days.

(21) Appl. No.: 13/800,518

(22) Filed: Mar. 13, 2013

(65) Prior Publication Data

US 2014/0018806 A1  Jan. 16, 2014

Related U.S. Application Data

(60) Provisional application No. 61/670,093, filed on Jul. 10, 2012.

(51) Int. Cl.
*A61B 17/72* (2006.01)
*A61B 17/92* (2006.01)
(Continued)

(52) U.S. Cl.
CPC ............... *A61B 17/921* (2013.01); *A61B 17/72* (2013.01); *A61B 17/7097* (2013.01); *A61B 17/7275* (2013.01); *A61B 17/8836* (2013.01); *A61B 2019/5466* (2013.01)
USPC .......................................................... 606/63

(58) Field of Classification Search
CPC ............ A61B 17/7097; A61B 17/7233; A61B 17/8836; A61B 2019/5466; A61B 2/4601; A61B 2/4603; A61B 2/4637; A61B 17/72; A61B 17/7275; A61B 17/921
USPC ............. 606/60, 62, 63, 79, 86 R, 92–95, 99, 606/86 A
See application file for complete search history.

(56) References Cited

U.S. PATENT DOCUMENTS

| 4,280,233 A | 7/1981 | Raab |
| 4,294,251 A | 10/1981 | Greenwald et al. |

(Continued)

FOREIGN PATENT DOCUMENTS

| DE | 40 28 466 | 3/1992 |
| EP | 0 709 698 | 5/1996 |

(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.
(Continued)

*Primary Examiner* — Pedro Philogene
*Assistant Examiner* — David Comstock
(74) *Attorney, Agent, or Firm* — Greenberg Traurig, LLP; David J. Dykeman; Roman Fayerberg

(57) ABSTRACT

Systems and methods for separating an internal bone fixation device from an introducer are disclosed. In some embodiments, a separation system includes a stabilizer configured to slide over an introducer for delivery of a bone fixation device to a bone cavity, the stabilizer being further configured to score a proximal end of the bone fixation device; and a separator configured to engage the introducer and to provide an impact to the introducer to separate the introducer from the bone fixation device.

23 Claims, 18 Drawing Sheets

(51) Int. Cl.
*A61B 17/70* (2006.01)
*A61B 17/88* (2006.01)
*A61B 19/00* (2006.01)

(56) References Cited

U.S. PATENT DOCUMENTS

| | | | |
|---|---|---|---|
| 4,313,434 A | 2/1982 | Segal |
| 4,341,691 A | 7/1982 | Anuta |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,562,598 A | 1/1986 | Kranz |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMicheal et al. |
| 4,888,024 A | 12/1989 | Powlan |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,085,660 A | 2/1992 | Lin |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,207,669 A | 5/1993 | Baker et al. |
| 5,295,733 A | 3/1994 | LeBegue |
| 5,295,962 A | 3/1994 | Crocker et al. |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,462,552 A | 10/1995 | Kiester |
| 5,480,400 A | 1/1996 | Berger |
| 5,538,514 A | 7/1996 | Hawkins |
| 5,548,676 A | 8/1996 | Savage, Jr. |
| 5,554,111 A | 9/1996 | Morrey et al. |
| 5,556,429 A | 9/1996 | Felt |
| 5,571,204 A | 11/1996 | Nies |
| 5,658,310 A | 8/1997 | Berger |
| 5,658,963 A | 8/1997 | Qian et al. |
| 5,705,181 A | 1/1998 | Cooper et al. |
| 5,707,374 A | 1/1998 | Schmidt |
| 5,713,901 A | 2/1998 | Tock |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 6,008,264 A | 12/1999 | Ostler |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,048,346 A | 4/2000 | Reiley et al. |
| 6,053,917 A | 4/2000 | Sherman et al. |
| 6,059,789 A | 5/2000 | Dinger et al. |
| 6,066,154 A | 5/2000 | Reiley et al. |
| 6,079,868 A | 6/2000 | Rydell |
| 6,103,203 A | 8/2000 | Fischer |
| 6,110,176 A | 8/2000 | Shapira |
| 6,121,341 A | 9/2000 | Sawhney et al. |
| 6,127,597 A | 10/2000 | Beyar et al. |
| 6,140,452 A | 10/2000 | Felt et al. |
| 6,159,236 A | 12/2000 | Biel |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,223,085 B1 | 4/2001 | Dann et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,258,089 B1 | 7/2001 | Campbell et al. |
| 6,261,289 B1 | 7/2001 | Levy |
| 6,280,456 B1 | 8/2001 | Scribner et al. |
| 6,282,013 B1 | 8/2001 | Ostler et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,332,894 B1 | 12/2001 | Stalcup et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,531 B2 | 7/2002 | Chen |
| 6,416,737 B1 | 7/2002 | Manolagas et al. |
| 6,419,483 B1 | 7/2002 | Adam et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,485,512 B1 | 11/2002 | Cheng |
| 6,494,883 B1 | 12/2002 | Ferree |
| 6,524,251 B2 | 2/2003 | Rabiner et al. |
| 6,524,313 B1 | 2/2003 | Fassier et al. |
| 6,551,321 B1 | 4/2003 | Burkinshaw et al. |
| 6,551,337 B1 | 4/2003 | Rabiner et al. |
| 6,565,528 B1 | 5/2003 | Mueller |
| 6,579,277 B1 | 6/2003 | Rabiner et al. |
| 6,579,279 B1 | 6/2003 | Rabiner et al. |
| 6,620,185 B1 | 9/2003 | Harvie et al. |
| 6,623,505 B2 | 9/2003 | Scribner et al. |
| 6,632,235 B2 | 10/2003 | Weikel et al. |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Rabiner et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |

(56) References Cited

U.S. PATENT DOCUMENTS

| | | |
|---|---|---|
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner et al. |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,757 B2 | 2/2012 | Zalenski et al. |
| 8,123,807 B2 | 2/2012 | Kim et al. |
| 8,210,729 B2 | 7/2012 | O'Leary et al. |
| 8,211,121 B1 | 7/2012 | Quinn et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,460 B2 | 5/2014 | Rabiner et al. |
| 2001/0011174 A1 | 8/2001 | Reiley et al. |
| 2001/0044626 A1 | 11/2001 | Reiley et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |

(56) References Cited

U.S. PATENT DOCUMENTS

| | | |
|---|---|---|
| 2007/0225705 A1 | 9/2007 | Osario et al. |
| 2007/0233146 A1 | 10/2007 | Henniges et al. |
| 2007/0255287 A1 | 11/2007 | Rabiner |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0082504 A1 | 4/2011 | Singhatt et al. |
| 2011/0098713 A1 | 4/2011 | Rabiner et al. |
| 2011/0110114 A1 | 5/2011 | Papac et al. |
| 2011/0118740 A1 | 5/2011 | Rabiner et al. |
| 2011/0160870 A1 | 6/2011 | Baumgartner et al. |
| 2011/0166306 A1 | 7/2011 | Stansbury et al. |
| 2011/0313356 A1 | 12/2011 | Rabiner et al. |
| 2012/0029102 A1 | 2/2012 | Rose et al. |
| 2012/0041557 A1 | 2/2012 | Frigg |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 99/43266 | 9/1999 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/039811 | 4/2008 |
| WO | WO 2008/063265 | 5/2008 |
| WO | WO 2009/059090 | 5/2009 |
| WO | WO 2009/064847 | 5/2009 |
| WO | WO 2009/082688 | 7/2009 |
| WO | WO 2009/088927 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO 2012/051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO2013/059609 | 4/2013 |
| WO | WO 2014/100427 | 6/2014 |

OTHER PUBLICATIONS

Maruyama et al., "Metacarpal Fracture Fixation with Absorbable Polyglycolide Rods and Stainless Steel K Wires: a Biomechanical Comparison", Journal of Biomedical Materials Research (Applied Biomaterials), vol. 33, Issue 1, pp. 9-12, Apr. 1996.

Waris et al., "Bioabsorbable Miniplating Versus Metallic Fixation for Metacarpal Fractures", Clinical Orthopaedics and Related Research, No. 410, pp. 310-319, May 2003.

Waris et al., "Self-Reinforced Bioabsorbable Versus Metallic Fixation Systems for Metacarpal and Phalangeal Fractures: a Biomechanical Study", The Journal of Hand Surgery, vol. 27A, No. 5, pp. 902-909, Sep. 2002.

PCT International Search Report based on PCT/US07/20402 dated Apr. 1, 2008.

PCT International Search Report based on PCT/US07/10050 dated Apr. 17, 2008.

PCT International Search Report based on PCT/US07/10038 dated Aug. 27, 2008.

PCT International Search Report based on PCT/US08/81929 dated Jan. 12, 2009.

PCT International Search Report based on PCT/US08/81924 dated Feb. 9, 2009.

PCT International Search Report based on PCT/US08/87630 dated Feb. 24, 2009.

(56) References Cited

OTHER PUBLICATIONS

PCT International Search Report based on PCT/US10/30275 dated Aug. 11, 2010.
PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
PCT International Search Report based on PCT/US11/66871 dated May 1, 2012.
USPTO Office Action in U.S. Appl. No. 11/789,906 mailed Apr. 29, 2009.
USPTO Office Action in U.S. Appl. No. 11/789,906 mailed Mar. 11, 2010.
USPTO Office Action in U.S. Appl. No. 11/789,906 mailed Apr. 30, 2010.
USPTO Office Action in U.S. Appl. No. 11/789,907 mailed May 11, 2010.
USPTO Office Action in U.S. Appl. No. 11/903,123 mailed Jul. 1, 2010.
USPTO Office Action in U.S. Appl. No. 11/964,370 mailed Dec. 9, 2010.
USPTO Office Action in U.S. Appl. No. 11/964,370 mailed Apr. 28, 2011.
USPTO Office Action in U.S. Appl. No. 11/964,370 mailed Sep. 23, 2011.
USPTO Office Action in U.S. Appl. No. 11/964,370 mailed Mar. 16, 2012.
USPTO Office Action in U.S. Appl. No. 12/262,411 mailed Sep. 1, 2010.
USPTO Office Action in U.S. Appl. No. 12/755,784 mailed Dec. 23, 2011.
USPTO Office Action in U.S. Appl. No. 12/756,014 mailed May 11, 2012.
USPTO Office Action in U.S. Appl. No. 12/858,924 mailed Oct. 24, 2011.
USPTO Office Action in U.S. Appl. No. 12/858,924 mailed Apr. 4, 2012.
USPTO Office Action in U.S. Appl. No. 12/875,460 mailed Mar. 8, 2012.
USPTO Office Action in U.S. Appl. No. 12/886,288 mailed Dec. 27, 2011.
USPTO Office Action in US U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/756,014 mailed Jan. 22, 2013.
USPTO Office Action in U.S. Appl. No. 13/088,916 mailed Jan. 23, 2013.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.
PCT International Search Report based on PCT/US13/49773 dated Oct. 1, 2013.
USPTO Office Action in U.S. Appl. No. 12/347,405 mailed Apr. 27, 2012.
USPTO Office Action in U.S. Appl. No. 13/772,947 mailed Jun. 19, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
USPTO Office Action in U.S. Appl. No. 13/617,557 mailed Oct. 9, 2013.
Extended European Search Report based on EP 10 76 2390 dated Oct. 30, 2013.
USPTO Office Action in U.S. Appl. No. 12/262,370 mailed Nov. 21, 2013.
USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
USPTO Office Action in U.S. Appl. No. 13/553,247 mailed May 7, 2014.
Extended European Search Report based on EP 14156473 dated May 13, 2014.
USPTO Office Action in U.S. Appl. No. 12/262,370 mailed Jun. 26, 2014.
USPTO Office Action in U.S. Appl. No. 13/617,557 mailed Jun. 27, 2014.
USPTO Office Action in U.S. Appl. No. 13/335,110 mailed Jul. 31, 2014.
USPTO Office Action in U.S. Appl. No. 13/616,781 mailed Aug. 26, 2014.
USPTO Office Action in U.S. Appl. No. 13/730,521 mailed Sep. 8, 2014.

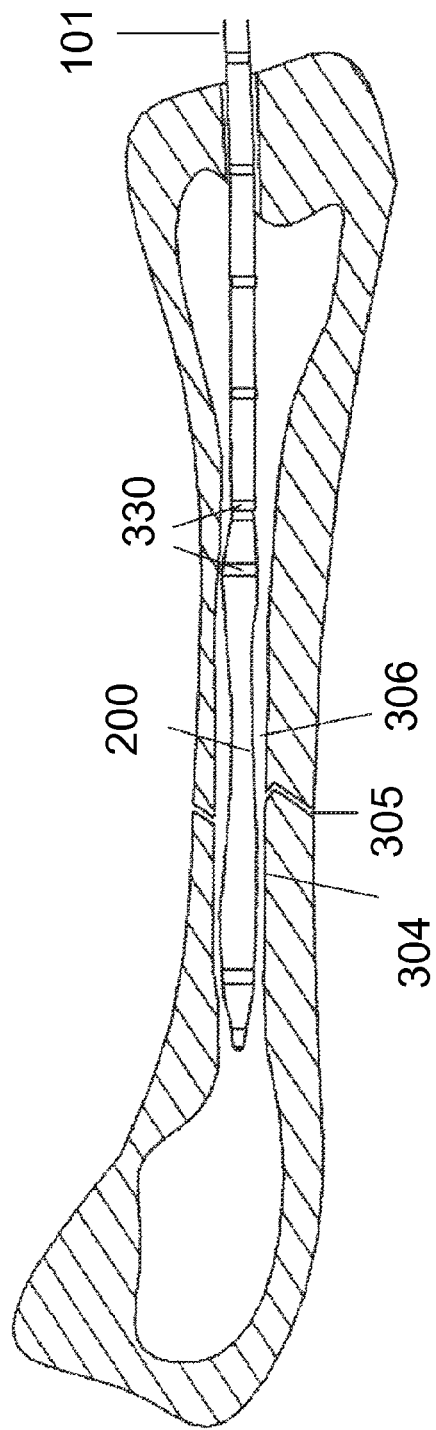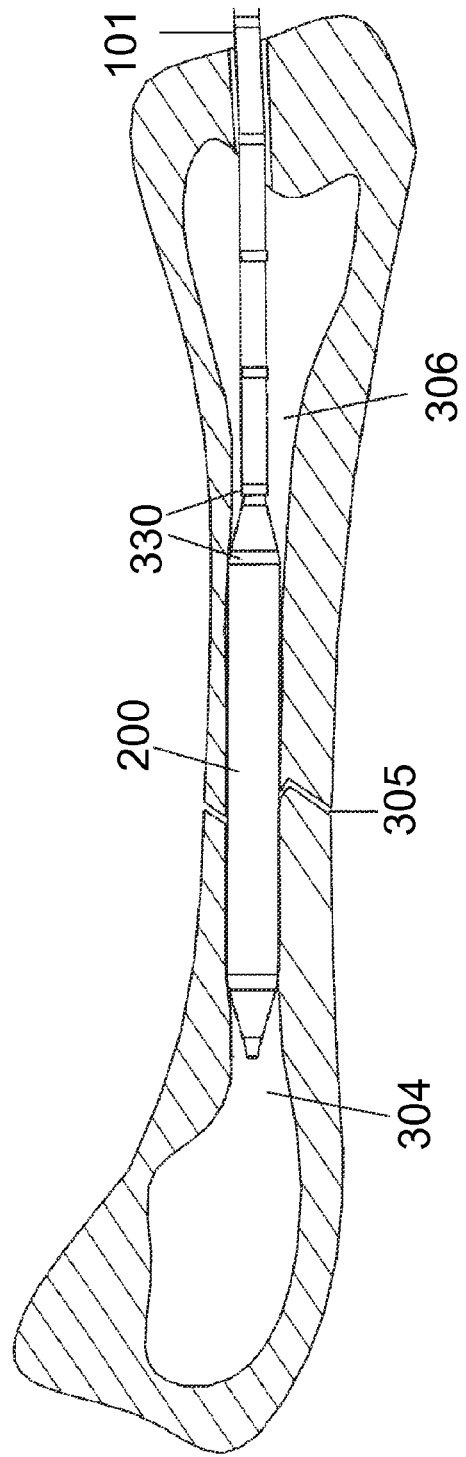

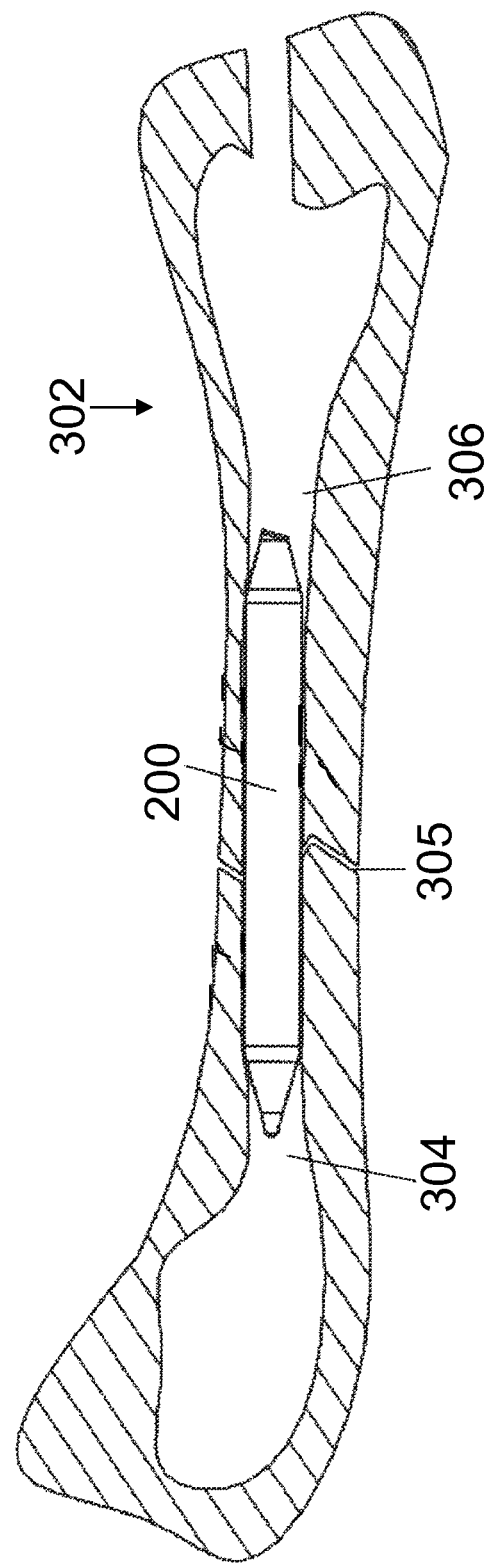

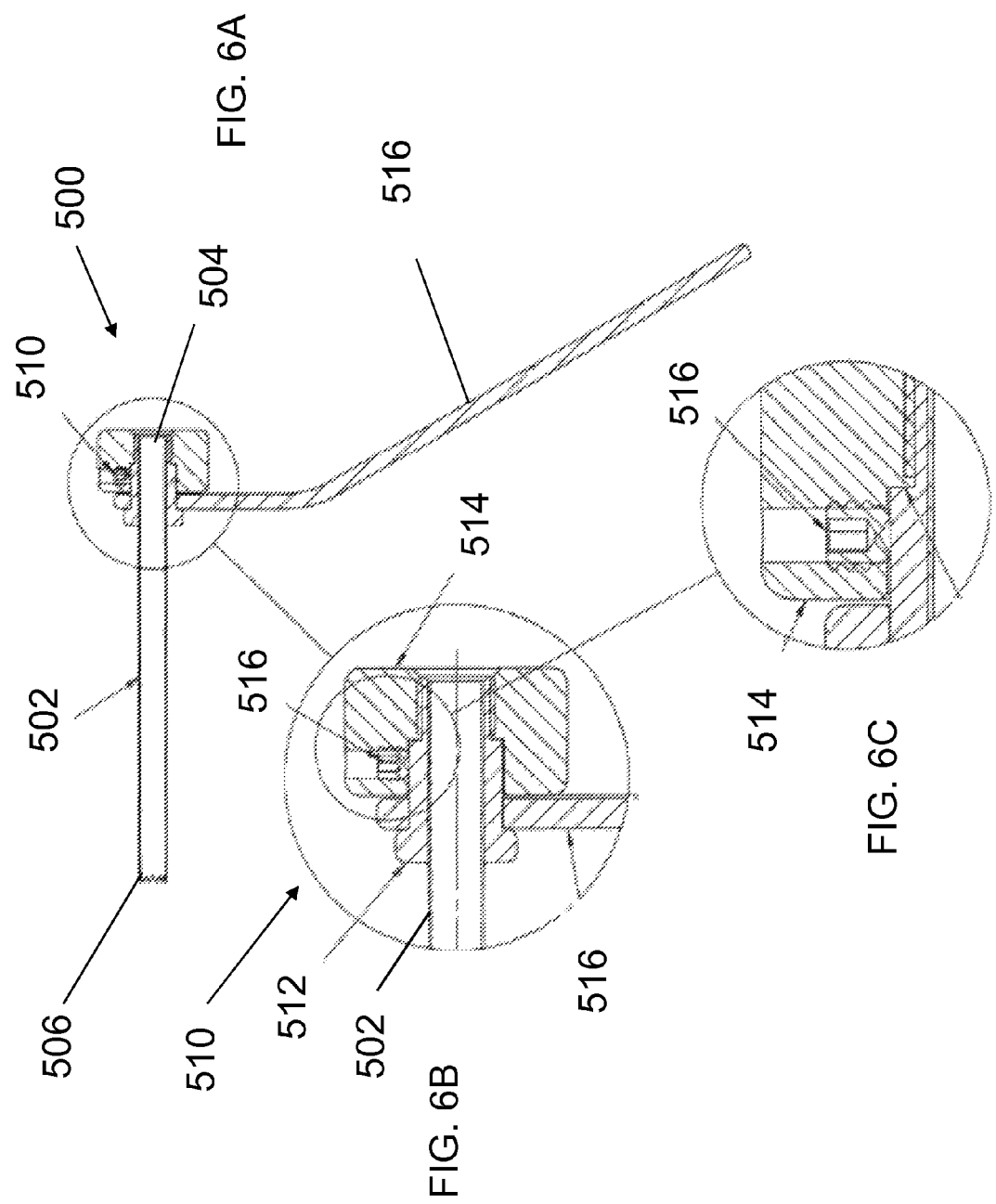

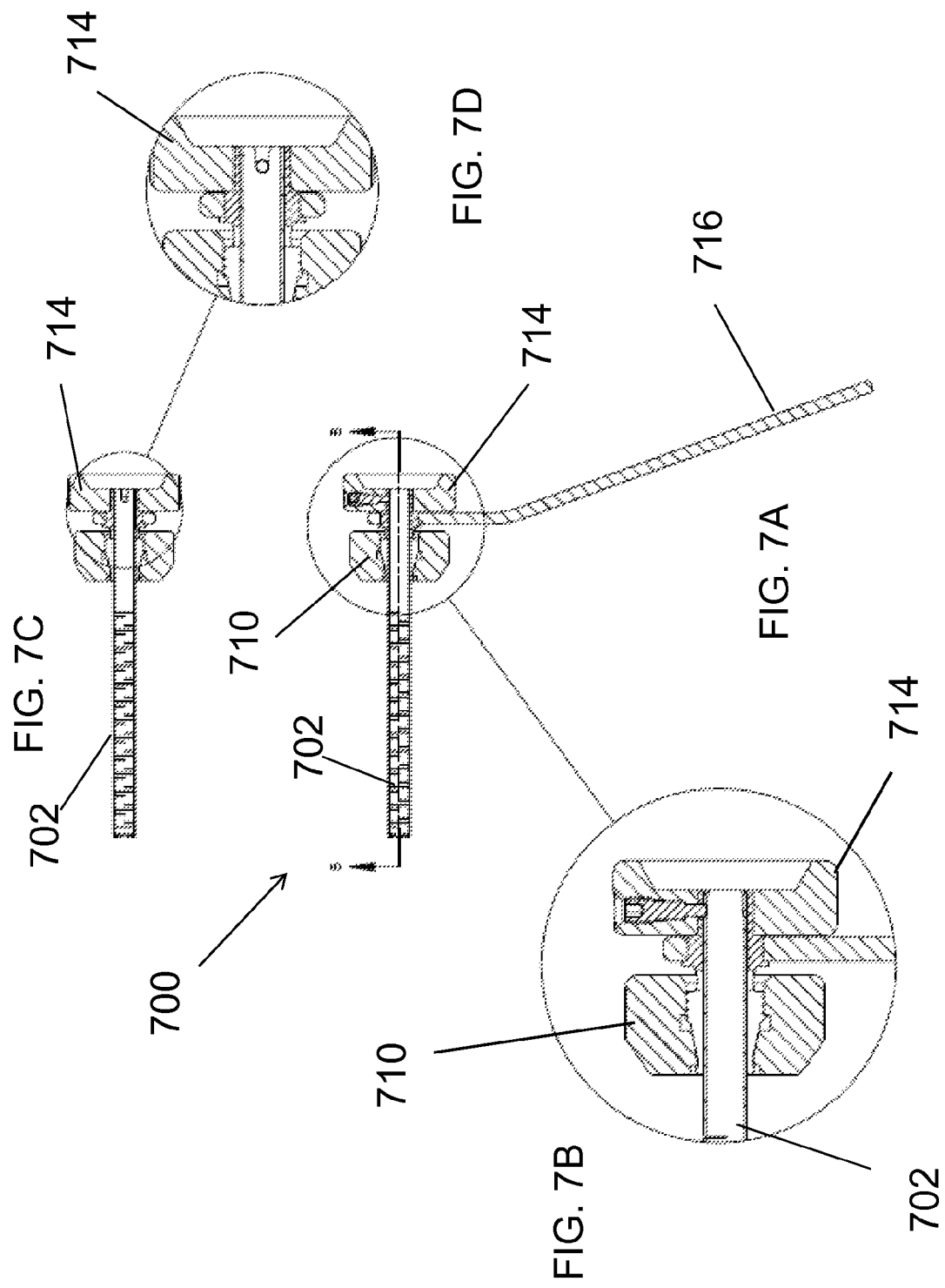

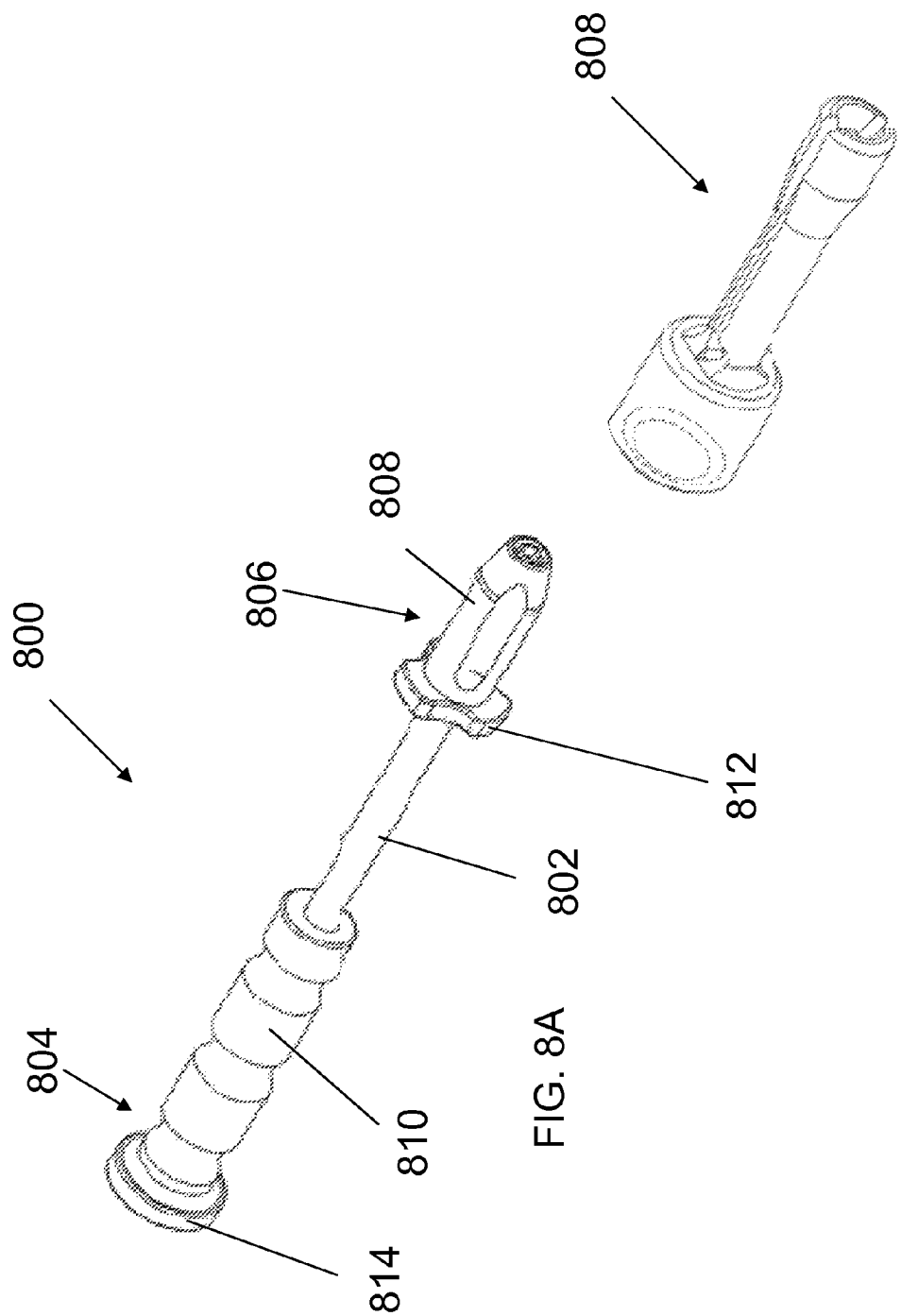

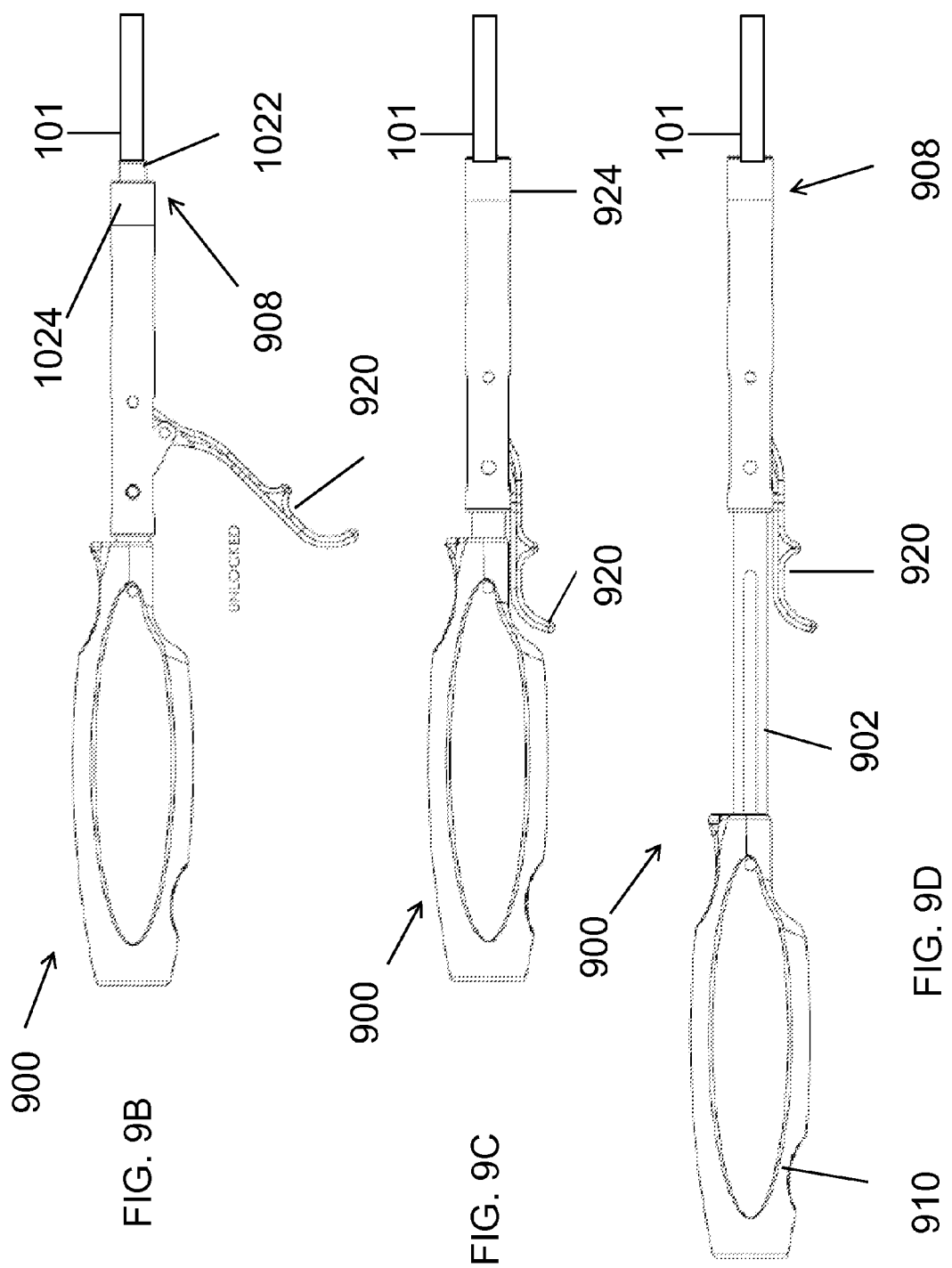

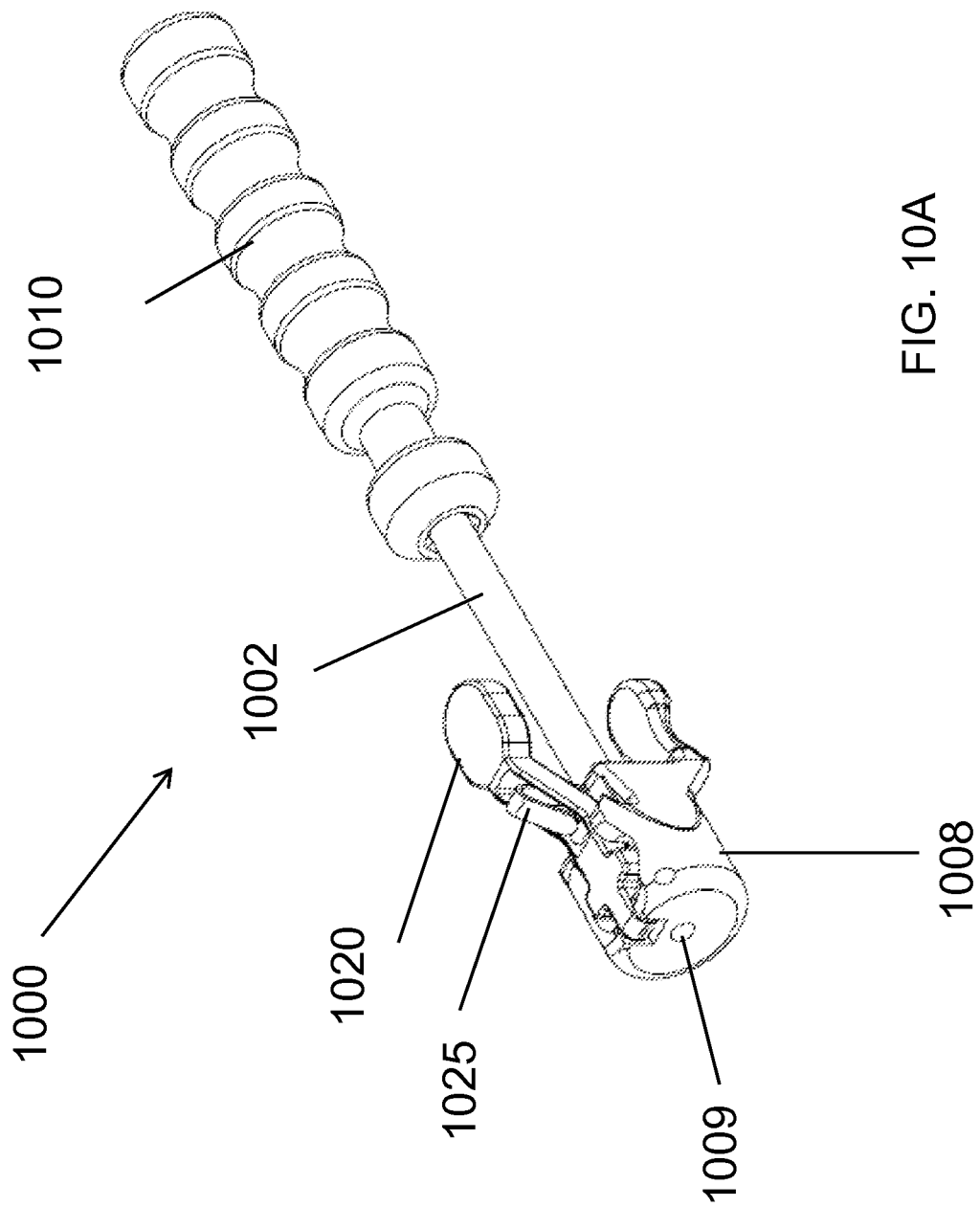

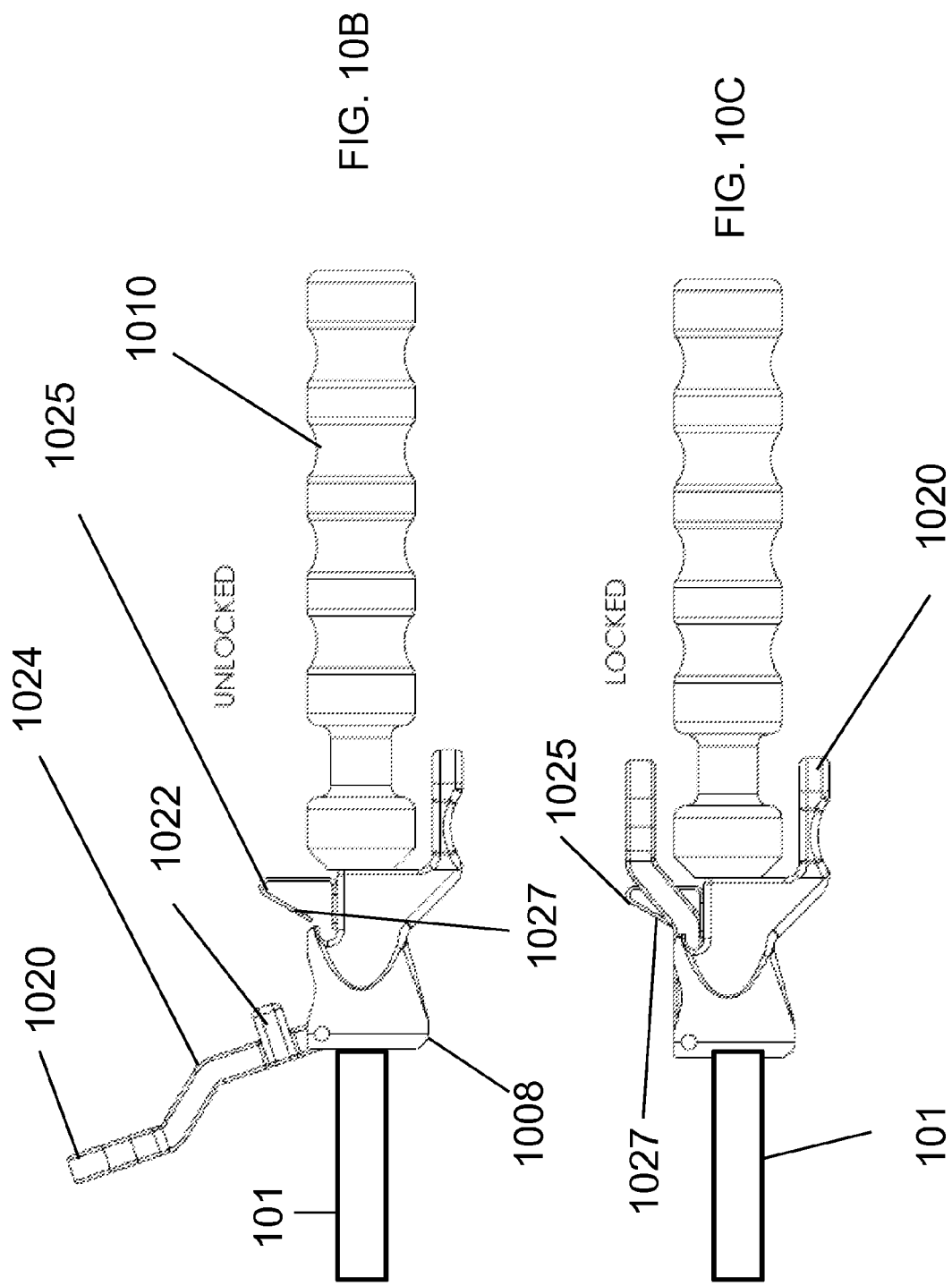

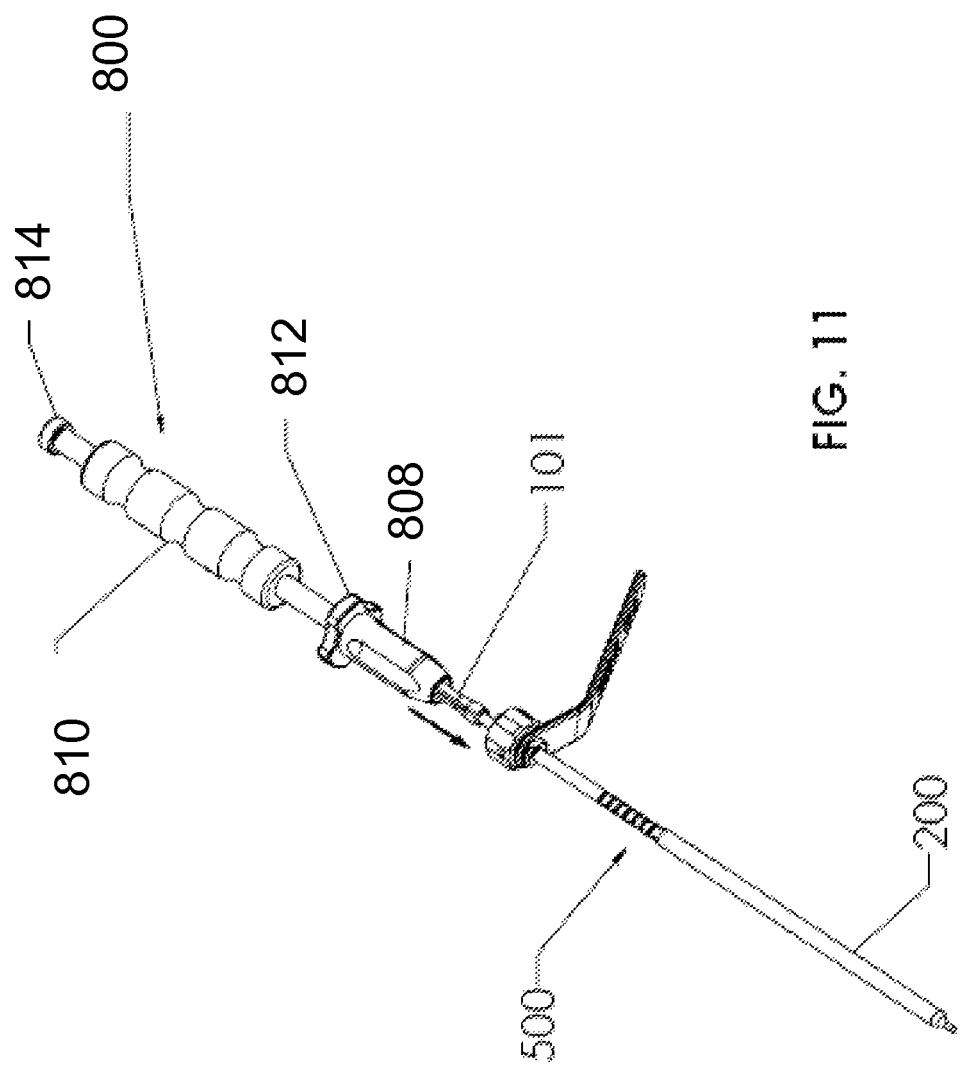

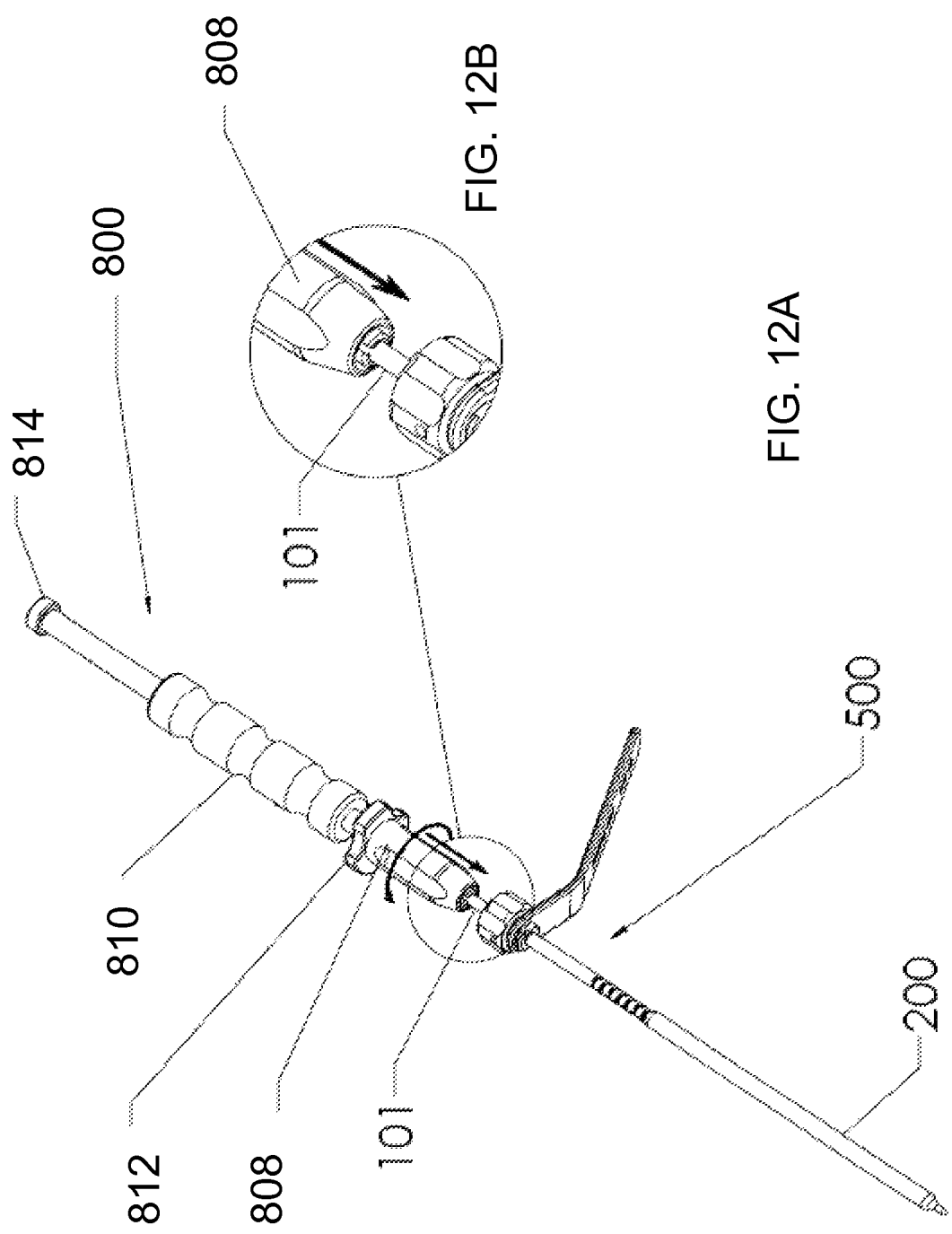

SYSTEMS AND METHODS FOR SEPARATING BONE FIXATION DEVICES FROM INTRODUCER

RELATED APPLICATIONS

This application claims the benefit of and priority to U.S. Provisional Application No. 61/670,093, filed on Jul. 10, 2012, and which is incorporated herein by reference in its entirety.

FIELD

The embodiments disclosed herein relate to systems and methods for use during an internal bone fixation procedure, and more particularly to systems and methods for separating an internal bone fixation device from an introducer.

BACKGROUND

Fracture repair is the process of rejoining and realigning the ends of broken bones. Currently there are several internal approaches to repair, strengthen and support a fractured bone. Conventional internal fixation devices include wires, plates, rods, pins, nails, and screws to support the fractured bone directly, as well as the addition of reinforcing materials to the fractured bone. Other internal fixation devices include expandable bone fixation devices in which an outer surface of the device contacts the interior surface of the medullary cavity which leads to greater support and strength to the healing bone. For example, one bone fixation device includes an expandable member that is placed within a cleared-out medullary cavity (void) of the fractured bone using an introducer that is releasably engaged to the expandable member. One challenge with inserting the internal bone fixation device in a bone is separating the device from the introducer. The force required to separate the device from the introducer should be minimal, thus allowing use by a wide variety of medical professionals. It would be desirable to have an improved system and method for separating the bone fixation device from an introducer.

SUMMARY

Systems and methods for separating bone fixation devices from an introducer are disclosed herein. In some aspects, there is provided a separation system that includes a stabilizer configured to slide over an introducer for delivery of a bone fixation device to a bone cavity, the stabilizer being further configured to score a proximal end of the bone fixation device; and a separator configured to engage the introducer and to provide an impact to the introducer to separate the introducer from the bone fixation device.

In some aspects, there is provided a separation system that includes an introducer having a distal end and a proximal end; a bone fixation device engaged to the distal end of the introducer; a stabilizer advanceable over the introducer to a proximal end of the bone fixation device, the stabilizer having a cutting distal edge to score the proximal end of the bone fixation device; and a separator having a shaft attachable to the proximal end of the introducer, and a hammer slidably disposed along the shaft to provide an impaction force on the introducer to separate the introducer from the bone fixation device.

In some aspects, there is provided a method of separating an internal bone fixation device from an introducer that includes forming an internal bone fixation device engaged to an introducer in an intramedullary cavity of a bone; scoring a proximal end of the internal bone fixation device; and providing an impact force on the introducer to separate the introducer from the bone fixation device.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A, FIG. 3B, FIG. 3C, and FIG. 3D show an embodiment of method steps for implanting an internal bone fixation device using an introducer that can be separated from the internal bone fixation device using the present systems and methods.

FIG. 3E shows an embodiment of an internal bone fixation device in a cavity of a bone after being separated from an introducer.

FIG. 6A illustrates an embodiment of a stabilizer of the present system.

FIG. 6B is a close-up of the circled area in FIG. 6A.

FIG. 6C is a close-up of the circled area in FIG. 6B.

FIG. 7A illustrates an embodiment of a stabilizer of the present system.

FIG. 7B is a close up view of the circled area of FIG. 7A.

FIG. 7C illustrates an embodiment of a stabilizer of the present system without a handle.

FIG. 7D is a close up view of the circled area of FIG. 7C.

FIG. 8A shows a perspective view of a slap hammer that may be used with the present system and method.

FIG. 8B is a perspective view of an embodiment of a chuck for use with the slap hammer shown in FIG. 8A.

FIG. 9B shows a perspective view of a slap hammer of FIG. 9A with the trigger in an open or unlocked position.

FIG. 9C shows a perspective view of a slap hammer of FIG. 9A with the trigger in a closed or unlocked position.

FIG. 9D shows a perspective view of a slap hammer of FIG. 9A with the trigger in a closed position and hammer in an activated position.

FIG. 10A shows a perspective view of a slap hammer having a trigger and a hammer of the present system.

FIG. 10B shows a perspective view of a slap hammer of FIG. 10A with the trigger in an open position.

FIG. 10C shows a perspective view of a slap hammer of FIG. 10A with the trigger in a closed position.

FIG. 11 shows an embodiment of the present system in operation.

FIG. 12A shows an embodiment of the present system in operation.

FIG. 12B is a close up of the circled area in FIG. 12A.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for using such systems during an internal bone fixation procedure are disclosed herein. The systems disclosed herein are used for separating an bone fixation device from an introducer. In some embodiments, during an internal bone fixation procedure, a first device such as a stabilizer may engage the introducer of a bone fixation system. The stabilizer may score the proximal end of the bone fixation device. The proximal end of the bone fixation device may be a separation area of a hardened internal bone fixation device. The system may include a second device such as a separator configured to engage a shaft of the introducer and provide an impact to the shaft of the introducer to separate the bone fixation device from the introducer.

The systems and methods disclosed herein can be used with any introducer. Suitable introducers include, but are not limited to, delivery or insertion catheters, flexible tubes, stents, or any other device that engages an internal bone fixation device and is able to position the internal bone fixation device into a medullary space of a fractured or weakened bone.

The systems and methods disclosed herein can be used with any suitable internal bone fixation device. Internal bone fixation devices include, but are not limited to, expandable internal bone fixation devices, such as a balloon. Any suitable expandable internal bone fixation devices may be used. Examples of expandable internal bone fixation devices include, but are not limited to, those devices described in U.S. Pat. No. 7,806,900, entitled "Apparatus and Method for Delivery of Reinforcing Materials to Bone" and U.S. Pat. No. 7,811,284, entitled "Systems and Methods for Internal Bone Fixation," which patents are incorporated herein by reference in their entireties.

By way of a non-limiting example, the systems and methods of the present disclosure are described in connection with separating an expandable portion from a flexible insertion catheter used for introducing the expandable portion into an intramedullary cavity of a bone. The systems and methods of the present disclosure may be applicable for separating other types of internal bone fixation devices from suitable introducers.

Figure 1:
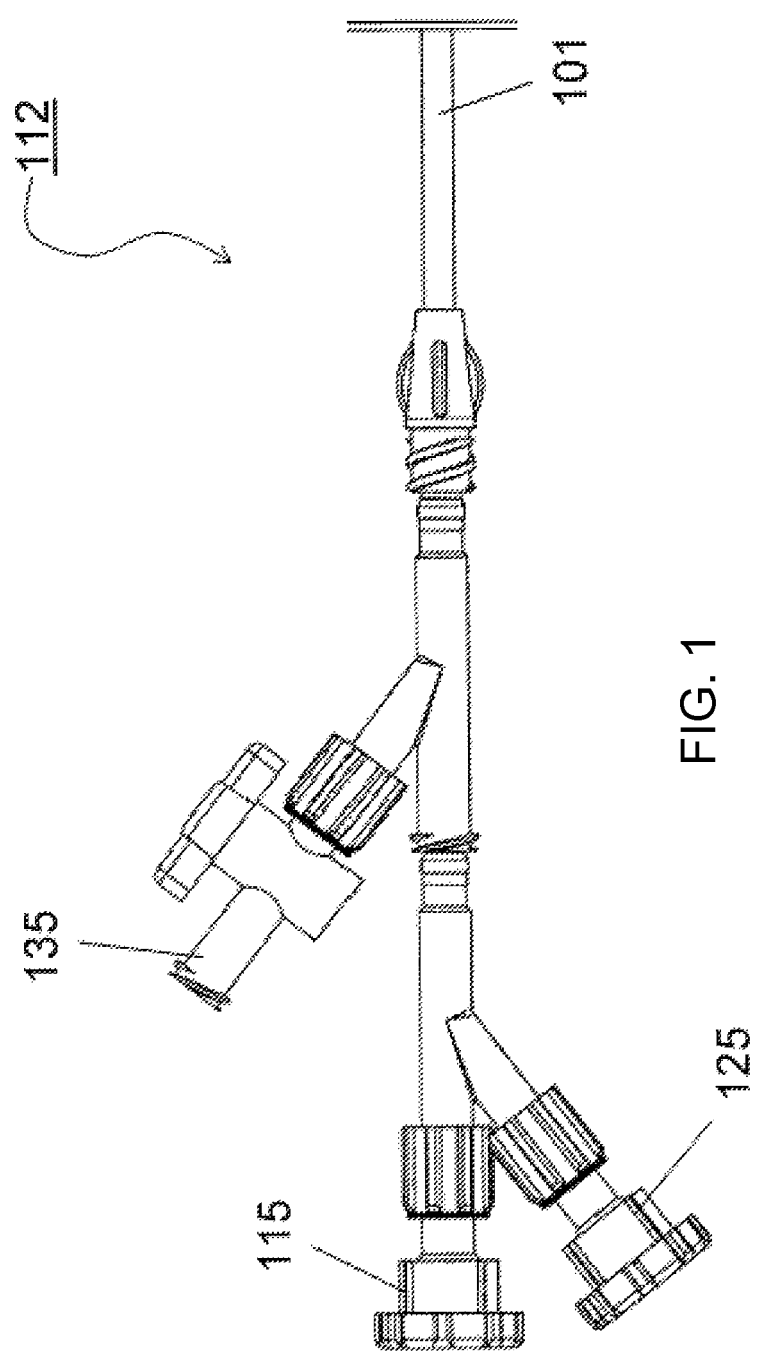
FIG. 1 is a side view of an embodiment of a proximal end of an introducer that can be separated from an internal bone fixation device using the present systems and methods.

FIG. 1 is a side view of an embodiment of a proximal end 112 of a flexible insertion catheter 101 for introduction of an expandable portion 200 into an intramedullary cavity of a bone to ultimately form a photodynamic bone fixation device. In some embodiments, the flexible insertion catheter 101 has an outer diameter from about 2 mm to about 8 mm. In some embodiments, the flexible insertion catheter 101 has an outer diameter from about 3 mm to about 6 mm.

Figure 2A:
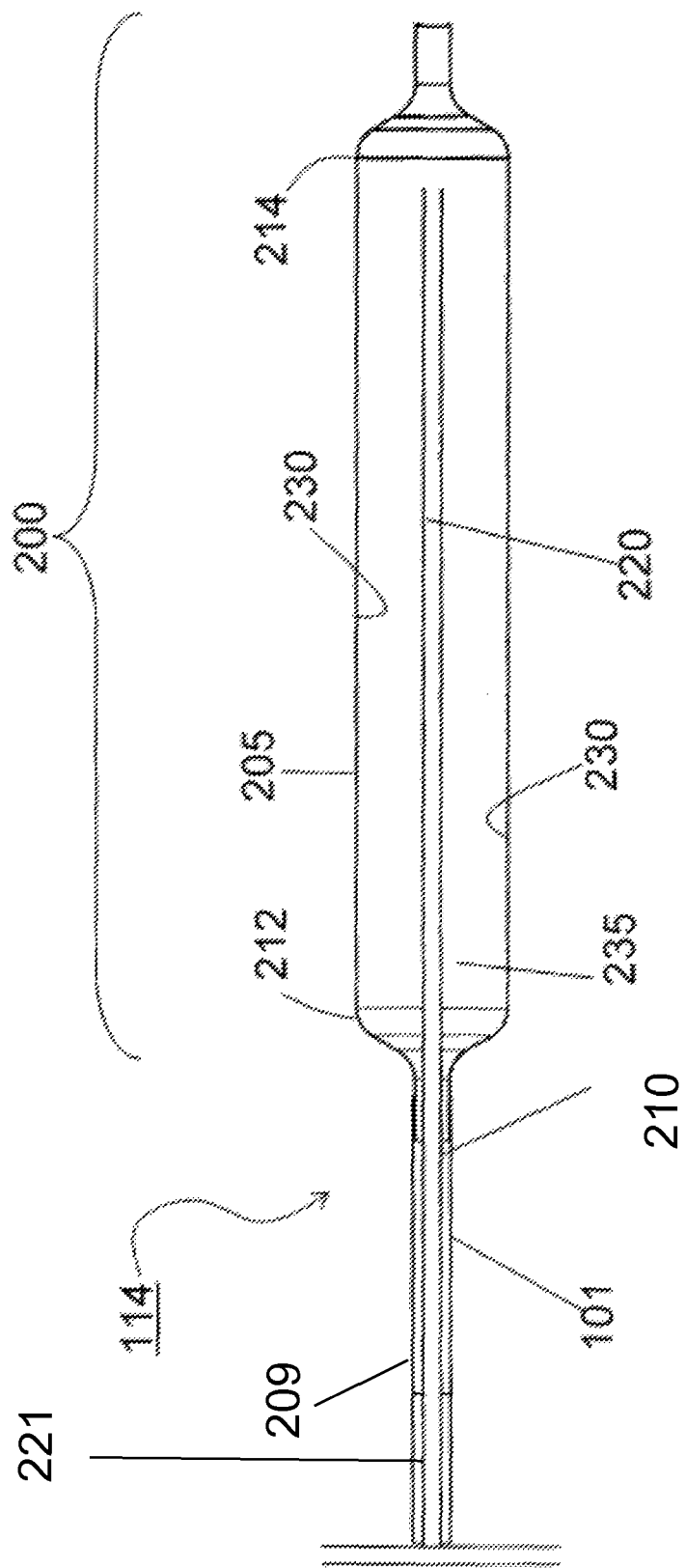
FIG. 2A is a side view of an embodiment of a distal end of an introducer for insertion of an internal bone fixation device of an intramedullary implant wherein the introducer can be removed using the present systems and methods.

FIG. 2A is a side view of an embodiment of a distal end 114 of the flexible insertion catheter 101. The distal end 114 includes the expandable portion 200 releasably mounted on the flexible insertion catheter 101. The expandable portion 200 has an outer surface 205, an inner surface 230, and an inner cavity 235 defined by the inner surface 230. In some embodiments, the expandable portion 200 is manufactured from a thin-walled, non-compliant (non-stretch/non-expansion) conformable material. The expandable portion 200 may be formed of a pliable, resilient, conformable, and strong material, including but not limited to urethane, polyethylene terephthalate (PET), nylon elastomer and other similar polymers. In some embodiments, the expandable portion 200 of the present disclosure is constructed out of a PET nylon aramet or other non-consumable materials. The expandable portion 200 may be impregnated with a radiopaque material to enhance the visibility of the expandable portion 200. The expandable portion 200 is biocompatible, thus preventing or reducing possible adverse reactions after insertion into a fractured bone. In some embodiments, the expandable portion 200 is made from a material that is non-toxic, non-antigenic and non-immunogenic. The expandable portion 200 includes a proximal area 212 and a distal area 214. The proximal area 212 of the expandable portion 200 is releasably connected to the distal end 114 of the insertion catheter 101.

In some embodiments, the insertion catheter may include multiple inner lumen or voids. For example, as shown in FIG. 2A, the insertion catheter may include an outer tube 209 having an inner void 210 therein for passing a light-sensitive liquid into the expandable portion and an inner tube 221 defining a central lumen 220 for passing a light-conducting fiber (which is not illustrated in FIG. 2A). The proximal end 112 of the flexible insertion catheter 101 includes at least two ports. In the embodiment shown in FIG. 1, the proximal end 112 includes three ports 115, 125, and 135. Port 115 can accept, for example, a light-conducting fiber. In some embodiments, the light-conducting fiber is an optical fiber. In some embodiments, the optical fiber has an outer diameter from about 1 mm to about 3 mm. The optical fiber is sized to pass through an inner lumen of the insertion catheter 101. The optical fiber can be made from any material, such as glass, silicon, silica glass, quartz, sapphire, plastic, combinations of materials, or any other material, and may have any diameter. In some embodiments, the optical fiber is made from a polymethyl methacrylate core with a transparent polymer cladding. It should be appreciated that the above-described characteristics and properties of the optical fibers are exemplary and not all embodiments of the present disclosure are intended to be limited in these respects. Port 125 can accept, for example, a syringe housing air or fluid. Port 135 can accept, for example, a syringe housing a light-sensitive liquid. In some embodiments, the light-sensitive liquid is a liquid monomer. In some embodiments, the syringe maintains a low pressure during the infusion and aspiration of the light-sensitive liquid. In some embodiments, the syringe maintains a low pressure of about 10 atmospheres or less during the infusion and aspiration of the light-sensitive liquid.

Light-sensitive liquid can be introduced into the proximal end 112 of the insertion catheter 101 and can pass through the inner void 210 of the insertion catheter 101 up into the inner cavity 235 of the expandable portion 200 to move the expandable portion from a deflated state to an inflated state when the light-sensitive liquid is delivered to the expandable portion, in order to form a rigid orthopedic stabilizer. In some embodiments, the light-sensitive liquid is provided as a unit dose. As used herein, the term "unit dose" is intended to mean an effective amount of light sensitive liquid adequate for a single session. By way of example, a unit dose of a light sensitive liquid of the present disclosure for expanding an expandable portion of the present disclosure may be defined as enough light-sensitive liquid to expand the expandable portion so that the expanded expandable portion realigns a fractured bone and/or secures the bone back into an anatomical position. The amount of realigning may vary somewhat from user to user. Thus, a user using a unit dose may have excess light-sensitive liquid left over. It is desirable to provide enough light-sensitive liquid that even the above-average user will have an effective amount of realignment. In some embodiments, a unit dose of a light-sensitive liquid of the present disclosure is contained within a container. In some embodiments, a unit dose of a light-sensitive liquid of the present disclosure is contained in an ampoule. In some embodiments, the expandable portion is sufficiently shaped to fit within a space or a gap in a fractured bone. In some embodiments, the light-sensitive liquid can be delivered under low pressure via a standard syringe attached to the port 135. The light-sensitive liquid can be aspirated and reinfused as necessary, allowing for adjustments to the expandable portion. These properties allow a user to achieve maximum fracture reduction prior to activating a light source and converting the liquid monomer into a hard polymer.

A light-conducting fiber communicating light from the light source can be introduced into the proximal end 112 of the insertion catheter 101 through port 115 and passes within an inner lumen of the insertion catheter 101 up into the expandable portion. In some embodiments, the light source emits frequency that corresponds to a band in the vicinity of 390 nm to 770 nm, the visible spectrum. In some embodiments, the light source emits frequency that corresponds to a band in the vicinity of 410 nm to 500 nm. In some embodiments, the light source emits frequency that corresponds to a band in the vicinity of 430 nm to 450 nm. The light-sensitive liquid remains a liquid monomer until activated by the light-conducting fiber (cures on demand). In some embodiments, the liquid monomer is exposed to an appropriate frequency of light and intensity to cure the monomer inside the expandable portion and form a rigid structure. In some embodiments, the liquid monomer is exposed to electromagnetic spectrum that is visible (frequency that corresponds to a band in the vicinity of 390 nm to 770 nm). In some embodiments, the liquid monomer is radiolucent, which permit x-rays to pass through the liquid monomer. Radiant energy from the light source is absorbed and converted to chemical energy to quickly (e.g., cured in about five seconds to about fifteen minutes) polymerize the monomer. This cure affixes the expandable portion in an expanded shape. A cure may refer to any chemical, physical, and/or mechanical transformation that allows a composition to progress from a form (e.g., flowable form) that allows it to be delivered through the inner void in the insertion catheter 101, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

Additives may be included in light-sensitive liquids, including, but not limited to, drugs (for example, antibiotics), proteins (for example, growth factors) or other natural or synthetic additives (for example, radiopaque or ultrasonically active materials). In some embodiments, the viscosity of the light-sensitive liquid has a viscosity of about 1000 cP or less. In some embodiments, the light-sensitive liquid has a viscosity ranging from about 650 cP to about 450 cP. The expandable portion may be inflated, trial fit and adjusted as many times as a user wants with the light-sensitive liquid, up until the light source is activated, when the polymerization process is initiated. Because the light-sensitive liquid has a liquid consistency and is viscous, the light-sensitive liquid may be delivered using low pressure delivery and high pressure delivery is not required, but may be used.

In some embodiments, a contrast material may be added to the light-sensitive liquid without significantly increasing the viscosity. Contrast materials include, but are not limited to, bismouth subcarbonate, barium sulfate, tantalum, or other contrast materials known in the art. The light-sensitive liquid can be introduced into the proximal end of the insertion catheter and passes within the inner void of the insertion catheter up into an inner cavity of the expandable portion to change a thickness of the expandable portion without changing a width or depth of the expandable portion. In some embodiments, the light-sensitive liquid is delivered under low pressure via the syringe attached to the port. The light-sensitive liquid can be aspirated and reinfused as necessary, allowing for thickness adjustments to the expandable body prior to activating the light source and converting the liquid monomer into a hard polymer. Low viscosity allows filling of the intramedullary implant through a very small delivery system.

One or more radiopaque markers or bands may be placed at various locations along the expandable portion 200 and/or the insertion catheter 101. A radiopaque ink bead may be placed at a distal end of the expandable portion for alignment of the apparatus during fluoroscopy. The one or more radiopaque bands and radiopaque ink bead, using radiopaque materials such as bismouth subcarbonate, barium sulfate, tantalum, or other materials known to increase radiopacity, allows a medical professional to view the apparatus using fluoroscopy techniques. The one or more radiopaque bands also provide visibility during inflation of the expandable portion to determine the precise positioning of the expandable portion during placement and inflation.

In some embodiments, the expandable portion 200 can have a length greater than about 300 mm and a diameter greater than about 20 mm. In such embodiments, there is the potential that during the curing of the light-sensitive liquid, a far distal area 214 of the expandable portion 200 may exhibit a shrinkage upon cure of about 2 to about 3 percent, while a proximal area 212 of the expandable portion 200 is being cured. In some embodiments, to prevent this from transpiring, the inner lumen 220 of the expandable portion 200 can be pressurized by virtue of the infusion of either air or other fluids (saline, water) through port 125 at the proximal end 112 of the insertion catheter 101. The infusion may cause internal diameter pressure against the light-sensitive liquid contained within the inner cavity 235 of the expandable portion 200 so that during the curing process, the pressure may keep the light-sensitive liquid pressurized, and up in contact with inner surface 230 of the expandable portion 200. When the light-conducting fiber is inserted within the inner lumen 220 and the light-sensitive liquid is infused, the extra space is pressed down on the inner lumen 220. In some embodiments, an expandable portion of the present disclosure has a diameter ranging from about 4 mm to about 30 mm. In some embodiments, an expandable portion of the present disclosure has a length ranging from about 20 mm to about 300 mm. An expandable portion of the present disclosure may be round, flat, cylindrical, oval, rectangular or any desired shape for a given application. In some embodiments, an expandable portion of the present disclosure has a diameter of about 4 mm and a length of about 30 mm. In some embodiments, an expandable portion of the present disclosure has a diameter of about 5 mm and a length of about 40 mm. In some embodiments, an expandable portion of the present disclosure has a diameter of about 6 mm and a length of about 30 mm. In some embodiments, an expandable portion of the present disclosure has a diameter of about 6 mm and a length of about 40 mm. In some embodiments, an expandable portion of the present disclosure has a diameter of about 6 mm and a length of about 50 mm. In some embodiments, an expandable portion of the present disclosure has a diameter of about 7 mm and a length of about 30 mm. In some embodiments, an expandable portion of the present disclosure has a diameter of about 7 mm and a length of about 40 mm. In some embodiments, an expandable portion of the present disclosure has a diameter of about 7 mm and a length of about 50 mm.

In some embodiments, an outer surface of an expandable portion of the present disclosure is resilient. In some embodiments, an outer surface of an expandable portion of the present disclosure is substantially even and smooth. In some embodiments, an outer surface of an expandable portion of the present disclosure is not entirely smooth and may have some small bumps or convexity/concavity along the length. In some embodiments, an outer surface of an expandable portion of the present disclosure may have ribs, ridges, projections, bumps or other shapes. In some embodiments, the ribs, ridges, projections, bumps, or other shapes on the rough or uneven outer surface of the expandable portion improve penetration of the at least one fastener into the expandable portion. In some embodiments, the ribs, ridges, projections, bumps, or other shapes on the rough or uneven outer surface of the expandable portion improve penetration of the at least one fastener into the expandable portion anywhere along a length of the expandable portion. In some embodiments, the ribs, ridges, projections, bumps, or other shapes on the rough or uneven outer surface of the expandable portion increase friction between the outer surface of the expandable portion and the at least one fastener so as to reduce slippage of the at least one fastener as the at least one fastener is driven towards the outer surface of the expandable portion. In some embodiments, the ribs, ridges, projections, bumps, or other shapes on the rough or uneven outer surface of the expandable portion interacts with a threaded portion of the at least one fastener so as to improve penetration and fastening of the at least one fastener into the expandable portion. In some embodiments, the ribs, ridges, projections, bumps, or other shapes on the rough or uneven outer surface of the expandable portion interact with a tip of the at least one fastener to improve the wedge ability of the tip of the fastener so as to decrease the driving force needed to penetrate the expandable portion. In some embodiments, an outer surface of an expandable portion of the present disclosure has an uneven geometry. In some embodiments, an outer surface of an expandable portion of the present disclosure has a textured surface which provides one or more ridges that allow grabbing. In some embodiments, the one or more ridges on the textured surface of the expandable portion allow grabbing of the at least one fastener so as to improve the penetration of the at least one fastener into the expandable portion. In some embodiments, the one or more ridges on the textured surface of the expandable portion allow grabbing of bone so as to improve adhesion between the expandable portion and bone as regenerating bone grows onto the outer surface of the expandable portion. In some embodiments, abrasively treating an outer surface of an expandable portion of the present disclosure for example via chemical etching or air propelled abrasive media improves the connection and adhesion between the outer surface of the expandable portion and a bone. The surfacing may significantly increase the amount of surface area that comes in contact with the bone resulting in a stronger grip. In some embodiments, the textured surface promotes bone growth onto the expandable portion. In some embodiments, the textured surface promotes bone growth of regenerating bone onto the outer surface of the expandable portion by grabbing the regenerating bone as it grows. In some embodiments, an expandable portion of the present disclosure is made by extruding material into a tube shape, and then forming the tube into a balloon. When forming the tube into the balloon, the balloon can be, for example, pre-stamped or milled to include a desired design, desired shape or surface modification. Then, the tube is heated and radially expanded via compressed air for a specific amount of time. The formed balloon is cooled and includes the desired design, desired shape or surface modification.

In some embodiments, an expandable portion of the present disclosure has an outer surface that is coated with materials such as drugs, bone glue, proteins, growth factors, or other coatings. For example, after a minimally invasive surgical procedure an infection may develop in a patient, requiring the patient to undergo antibiotic treatment. An antibiotic drug may be added to an outer surface of an expandable portion of the present disclosure to prevent or combat a possible infection. Proteins, such as, for example, bone morphogenic protein or other growth factors have been shown to induce the formation of cartilage and bone. In some embodiments, a growth factor is added to an outer surface of an expandable portion of the present disclosure to help induce the formation of new bone. In some embodiments, as the formation of new bone is induced the new bone interacts with a textured outer surface of the expandable portion so that new bone is formed onto the textured outer surface of the expandable portion. Due to the lack of thermal egress of light-sensitive liquid in an expandable portion of the present disclosure, the effectiveness and stability of the coating is maintained.

In some embodiments, a stiffness of any of the expandable portion of the present disclosure can be increased due to the presence of external stiffening members or internal stiffening members. In some embodiments, a wrapping, sheathing or an attachment of Nitinol or other metallic memory-type metal piece(s) are aligned in a longitudinal fashion, with multiple rods being placed circumferentially around the expandable portion so as to have these metallic pieces change their configuration under a temperature change. In some embodiments, an inner surface of the metallic pieces (those surfaces that are in contact with the external circumferential surface of the intramedullary implant) are polished to increase internal reflection of the light from the light-conducting fiber. The metallic pieces are designed to be load-bearing shapes. In some embodiments, the metallic pieces have a low profile and can handle large loads. In some embodiments, metallic pieces may be positioned on the external circumferential surface of an expandable portion. The metallic pieces can be aligned in a longitudinal fashion, circumferentially around the expandable portion and can be interconnected with one another via connecting means such as wires. The wires will help hold the longitudinal metallic pieces in position. In some embodiments, the metallic pieces expand to increase the strength of the hardened expandable portion. In some embodiments, the metallic pieces contract to increase the strength of the hardened expandable portion. In some embodiments, metallic pieces are positioned on an internal circumferential surface of an expandable portion. In some embodiments, two metallic memory-type metal wires, such as Nitinol, are positioned within an expandable portion. Heat from a light-conducting fiber makes the metal wires get smaller, tensioning the hardened expandable portion. In some embodiments, heat from a light-conducting fiber and reaction with the polymerization process, makes the metal wires get smaller, tensioning the hardened expandable portion. In some embodiments, an expandable portion is wrapped with a plurality of flat metallic plates that move into a corrugated or other shape upon a temperature change to increase the strength of the previously flat metal plate into a shape capable of handling a load. In some embodiments, the metals are rectangular, semicircular, hexagonal, or triangular in section, although not all embodiments are limited to these shapes.

An expandable portion typically does not have any valves. One benefit of having no valves is that the expandable portion may be inflated or deflated as much as necessary to assist in the fracture reduction and placement. Another benefit of the expandable portion having no valves is the efficacy and safety of the implant. Since there is no communication passage of light-sensitive liquid to the body there cannot be any leakage of liquid because all the liquid is contained within the expandable portion. In some embodiments, a permanent seal is created between the expandable portion that is both hardened and affixed prior to the insertion catheter 101 being removed. The expandable portion may have valves, as all of the embodiments are not intended to be limited in this manner.

In some embodiments, an expandable portion of the present disclosure includes a pathway sufficiently designed for passing a cooling medium. Once the expandable portion is expanded, a cooling media may be delivered within (via an internal lumen) or around (via external tubing) the expandable portion in order to prevent the possibility of overheating. Medium used for cooling includes, but is not limited to, gases, liquids and combinations thereof. Examples of gases include, but are not limited to, inert gases and air. Examples of liquids include, but are not limited to, water, saline, saline-ice mixtures, liquid cryogen. In some embodiments, the cooling media is water. The cooling media can be delivered to the expandable portion at room temperature or at a cooled temperature. In some embodiments, the cooling media improves the numerical aperture between that of the light-conducting fiber and the inner lumen for the light-conducting fiber because any air existing between the light-conducting fiber and the material of the expandable portion is taken away so as to improve light transmission. Therefore, the light transmission will be light-conducting fiber—cooling media—expandable portion—light-sensitive liquid as opposed to light-conducting fiber—air—expandable portion—light-sensitive liquid. In some embodiments, the cooling media transmitted through the inner lumen of the expandable portion takes away extraneous heat. In some embodiments, no cooling media is used.

In some embodiments, the inner lumen of the expandable portion penetrates through a distal end of the expandable portion for cooling through the length of the expandable portion. In some embodiments, the inner lumen has a return flow path for cooling. In some embodiments, the inner lumen is pressurized to move the cooling media in the inner lumen. In some embodiments, the expandable portion has external helical tubing for providing cooling media to the expandable portion.

In some embodiments, a light-conducting fiber can be introduced into the inner lumen of the expandable portion and activated to cure the light-sensitive liquid, while a cooling medium may flow through the inner lumen and out the distal end of the expandable portion.

In some embodiments, a separation area is located at the junction between the expandable portion and the insertion catheter. The separation area may have a stress concentrator. The stress concentrator may be a notch, groove, channel or similar structure that concentrates stress in the separation area. The stress concentrator of the separation area may be notched, scored, indented, pre-weakened or pre-stressed to direct separation of the expandable portion from the elongated shaft of the insertion catheter under specific torsional load. The separation area ensures that there are no leaks of the light-sensitive liquid from the insertion catheter and/or the expandable portion. The separation area seals the expandable portion and removes the insertion catheter by making a break at a known or predetermined site (e.g., a separation area). The separation area may be various lengths and up to about an inch long. In some embodiments, when torque (twisting) is applied to the insertion catheter, the shaft of the insertion catheter separates from the expandable portion. The system of the present disclosure may be used to separate the expandable portion 200 from the insertion catheter 101 at the separation area.

Figure 2B:
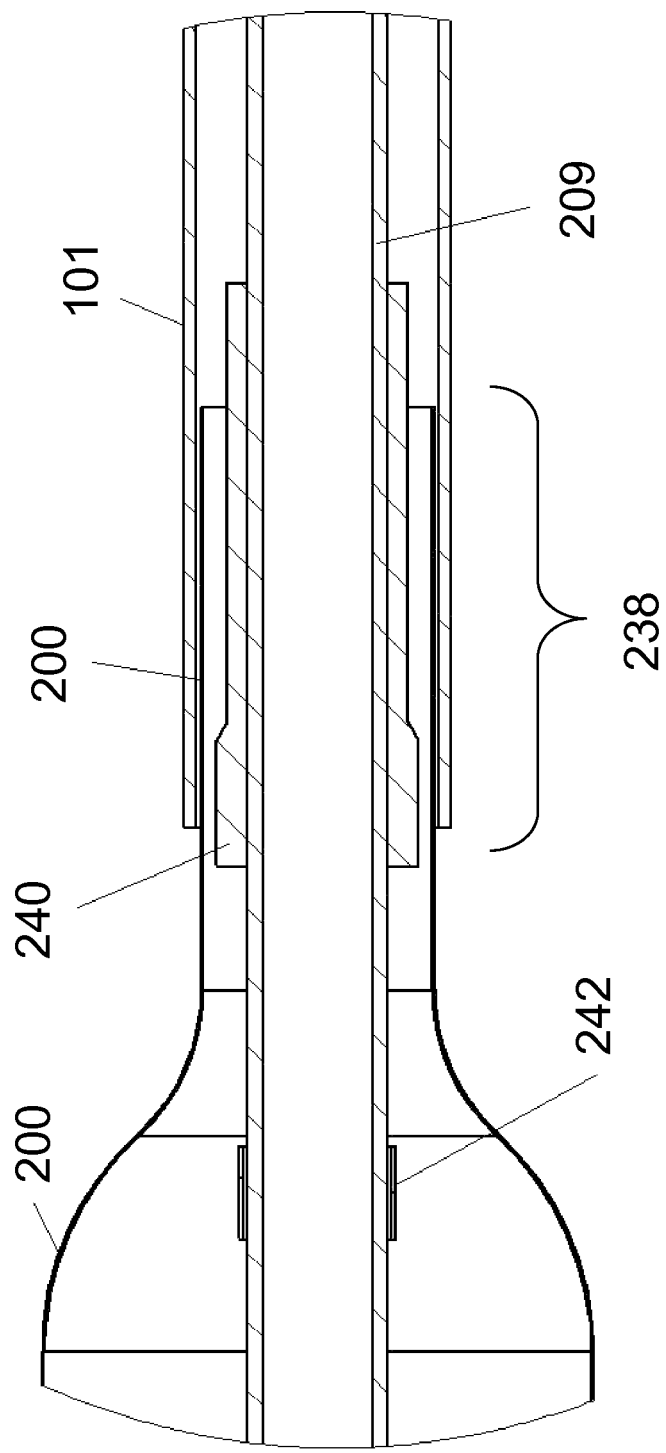
FIG. 2B is a side view of an embodiment of a separation area where an internal bone fixation device and an introducer may be separated using the present systems and methods.

FIG. 2B is a close up of an embodiment separation area 238 between the expandable portion and the flexible insertion catheter 101. The separation area may include a restrictor 240. The restrictor may be configured to concentrate the separation force close to the proximal area 212 of the expandable portion 200 so that the entire insertion catheter 101 may be removed. The restrictor 240 may be any mechanism that can decrease the diameter of the expandable portion 200 in the region of the restrictor 240. It may be desirable to restrict the diameter of the expandable portion 200 in the region of the restrictor so that when the light-sensitive liquid is cured, a weakened or thinned section of the cured light-sensitive liquid is created between the expandable portion 200 and the insertion catheter 101 around the separation area so that upon impact force on the insertion catheter 101, the separation of the expandable portion 200 and the insertion catheter occurs at the restrictor 240. The restrictor 240 may be of any suitable dimensions or shapes. For example, the restrictor may be straight or tapered. For example, the restrictor may be a sleeve, sheath, tube, or any other additional material that may be applied to the insertion catheter 101 to reduce the diameter of the expandable portion 200. The restrictor 240 may be applied to the insertion catheter 101 using any suitable means including, for example, applying an adhesive such as glue. The restrictor may be made from the same material as the expandable portion 200. In some embodiments, the restrictor 240 may be disposed around the inner tube 209 between the expandable portion 200 and the inner tube 209 to decrease the amount of light-sensitive material in the expandable portion 200 about the separation area. As shown in FIG. 2B, one or more radiopaque markers 242 may be placed on the inner tube 209.

Figure 3A:
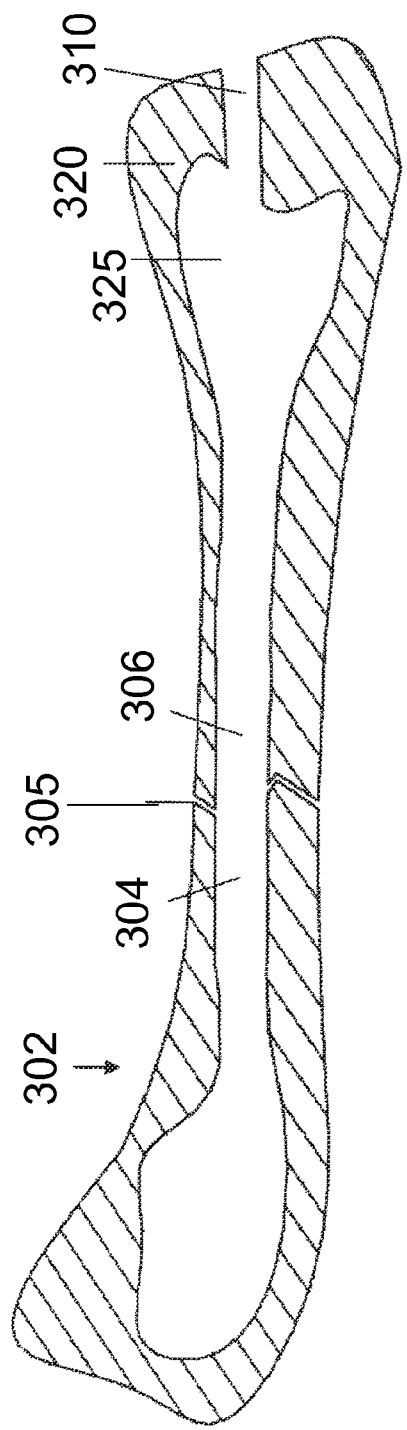

FIG. 3A, FIG. 3B, FIG. 3C, FIG. 3D and FIG. 3E, in combination with FIG. 1, FIG. 2A and FIG. 2B, illustrate an embodiment of method steps for implanting an expandable portion of an intramedullary implant of the present disclosure within the intramedullary space of a weakened or fractured bone. A minimally invasive incision (not shown) may be made through the skin of the patient's body to expose a fractured bone 302. The incision may be made at the proximal end or the distal end of the fractured bone 302 to expose the bone surface. Once the bone 302 is exposed, it may be necessary to retract some muscles and tissues that may be in view of the bone 302. As shown in FIG. 3A, an access hole 310 may be formed in the bone by drilling or other methods known in the art. In some embodiments, the access hole 310 has a diameter of about 3 min to about 10 mm. In some embodiments, the access hole 310 has a diameter of about 3 mm.

The access hole 310 extends through a hard compact outer layer 320 of the bone into the relatively porous inner or cancellous tissue 325. For bones with marrow, the medullary material should be cleared from the medullary cavity prior to insertion of the inventive device. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

Figure 3B:
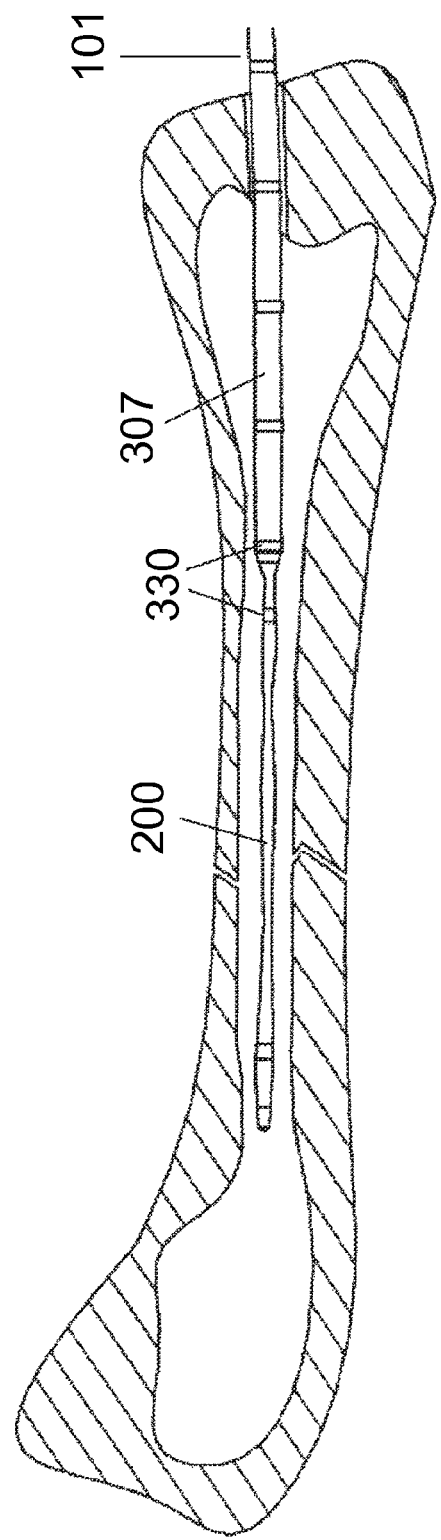

A guidewire (not shown) may be introduced into the bone 302 via the access hole 310 and placed between bone fragments 304 and 306 of the bone 302 to cross the location of a fracture 305. The guidewire may be delivered into the lumen of the bone 302 and may cross the location of the break 305 so that the guidewire spans multiple sections of bone fragments. As shown in FIG. 3B, the expandable portion 200 of the insertion catheter 101 for repairing a fractured bone is delivered to the site of the fracture 305 and spans the bone fragments 304 and 306 of the bone 302. In some embodiments, a guidewire may be placed into the intramedullary cavity of the bone and a sheath, with assistance from ad dilator, combination may be advanced over the guidewire. Once the sheath is inside the intramedullary cavity, the guidewire and dilator can be withdrawn. Next, the expandable portion 200 may be placed into the sheath, which can be removed to leave the expandable portion 200 in place inside the intramedullary cavity. The location of the expandable portion 200 may be determined using at least one radiopaque marker 330 which is detectable from the outside or the inside of the bone 302. Once the expandable portion 200 is in the correct position within the fractured bone 302, a delivery system which contains a light-sensitive liquid is attached to the port 135. The light-sensitive liquid is then infused through the inner void 210 in the delivery catheter 101 and enters the inner cavity 235 of the expandable portion 200. This addition of the light-sensitive liquid within the expandable portion 200 causes the expandable portion 200 to expand, as shown in FIG. 3C. As the expandable portion 200 is expanded, the fracture 305 is reduced. Unlike traditional implants, such as rods, that span the fracture site, the expandable portion 200 of the present disclosure does more than provide longitudinal strength to both sides of the fractured bone. In some embodiments, the expandable portion 200 having the design can be a spacer for reducing the fracture and for holding the fractured and compressed bones apart at the point of the collapsed fracture.

Once orientation of the bone fragments 304 and 306 are confirmed to be in a desired position, the light-sensitive liquid may be hardened within the expandable portion 200, as shown in FIG. 3D, such as by illumination with a visible emitting light source. In some embodiments, during the curing step, a syringe housing a cooling media may be attached to the proximal end of the insertion catheter and continuously delivered to the expandable portion 200. The cooling media can be collected by connecting tubing to the distal end of the inner lumen and collecting the cooling media via the second distal access hole. After the light-sensitive liquid has been hardened, the light source may be removed from the device. Alternatively, the light source may remain in the expandable portion 200 to provide increased rigidity.

FIG. 3E shows an embodiment of an internal bone fixation device in a cavity of a bone after being separated from an introducer. For example, the expandable portion 200 once hardened, may be released from the delivery catheter 101 using the present systems and methods to form a photodynamic bone fixation device inside the intramedullary cavity of the bone 302.

An embodiment of a system for the separation of an internal bone fixation device from an introducer is shown in the various illustrations of FIGS. 4-10.

Figure 4:
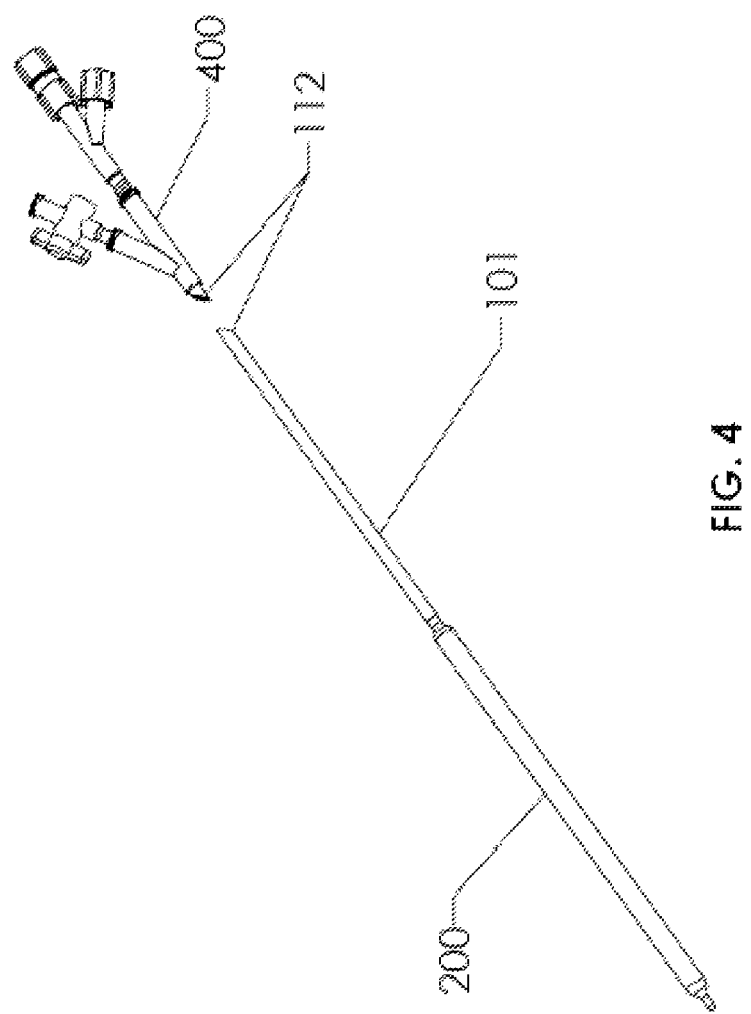
FIG. 4 shows a perspective view of an embodiment of a Y-connector of an introducer separated from the remainder of the introducer.

Referring to FIG. 4, to begin separating the expandable portion 200 from the insertion catheter 101, the proximal end 112 of the insertion catheter 101 may be uncovered to allow one or more devices for separation of the expandable portion 200 from the insertion catheter 101 to be advanced over the insertion catheter 101. In some embodiments, the Y-connector 400 may be cut off from the insertion catheter 101 to uncover the proximal end 112 of the insertion catheter 101. The Y-connector 400 may be separated from the remainder of the insertion catheter 101 using any suitable method or mechanism. For example, the Y-connector 400 may be cut off using surgical scissors, a scalper or a similar cutting instrument.

Figures 5A, 5B:
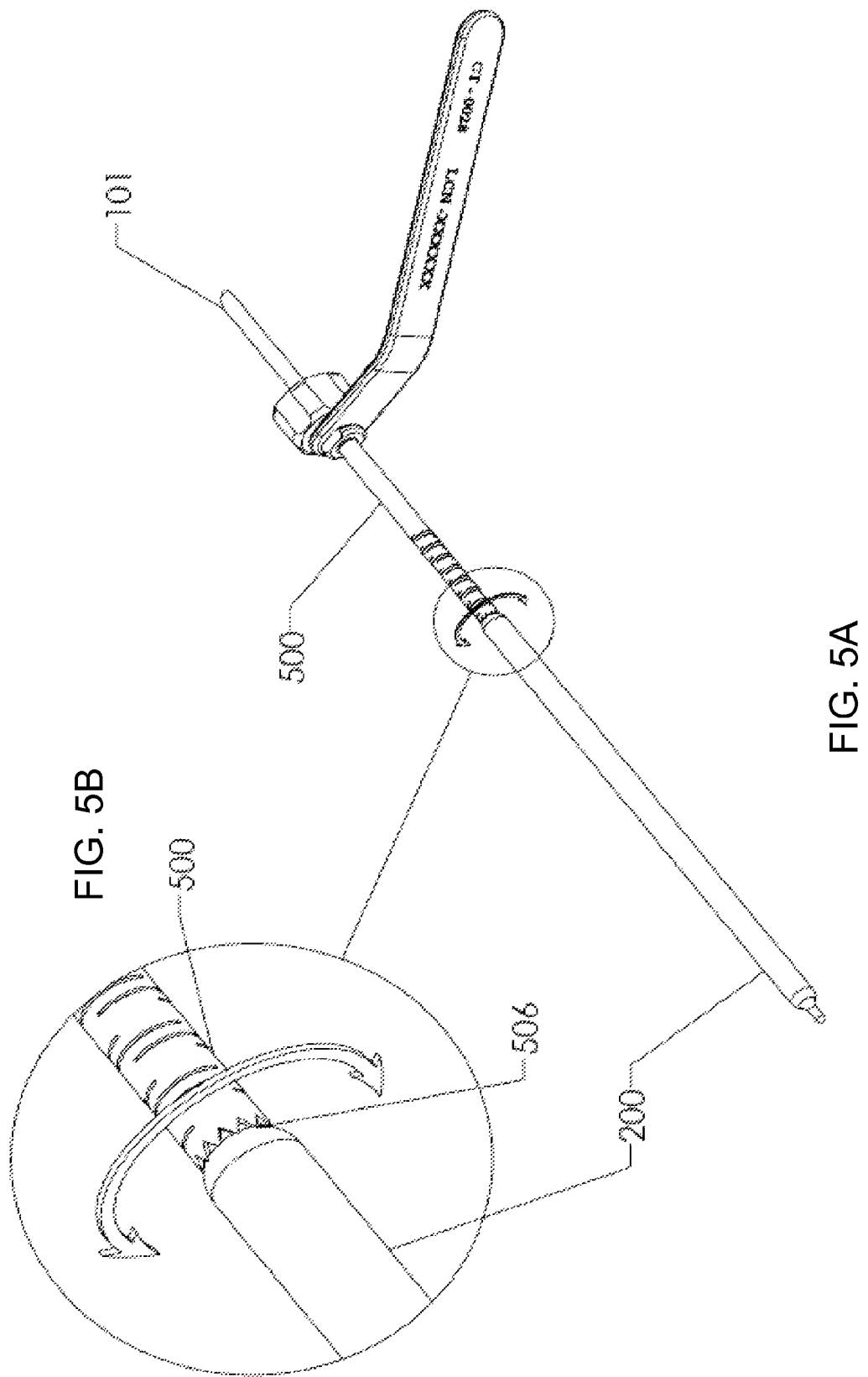
FIG. 5A shows a perspective view of an embodiment of a stabilizer of the present system engaging an internal bone fixation device.
FIG. 5B is a close-up of the circled area in FIG. 5A.

Referring to FIG. 5A and FIG. 5B, once the proximal end 112 of the insertion catheter 100 has been uncovered, a stabilizer 500 may be slid over the insertion catheter until a distal end 506 of the stabilizer 500 is pressed against the proximal end of the expandable portion 200. The stabilizer 500 may stabilize the insertion catheter 101 and the expandable portion 200 during the separation of the expandable portion 200 from the insertion catheter 101, as described below. In some embodiments, the stabilizer 500 scores the proximal end of the expandable member 200 to facilitate the subsequent separation of the expandable member 200 from the insertion catheter 101. The scoring and cutting may be done along the restrictor 240 to facilitate separation of the expandable portion 200 from the insertion catheter 101 at the restrictor 240.

FIG. 6A illustrates an embodiment of the stabilizer 500. As generally shown in FIG. 6A, the stabilizer 500 may include a tube assembly 502 having an internal lumen to allow the tube assembly 502 to slide over the insertion catheter 101. The tube assembly has a proximal end 504 and a distal end 506, which, in some embodiments, may be serrated. In some embodiments, the tube assembly 502 may be rigid or may have a flexible distal region depending, for example, on the angle of the access hole in the bone being fixated and also the depth of the expandable member 200. In some embodiments, the tube assembly 502 may be provided with a flexible distal portion by a variety of techniques, including, but not limited to, using any suitable flexible material, such as plastic, Nitinol or other shape memory material, laser cutting, using a wound wire or spring-like device, and other suitable techniques.

Figure 6D:
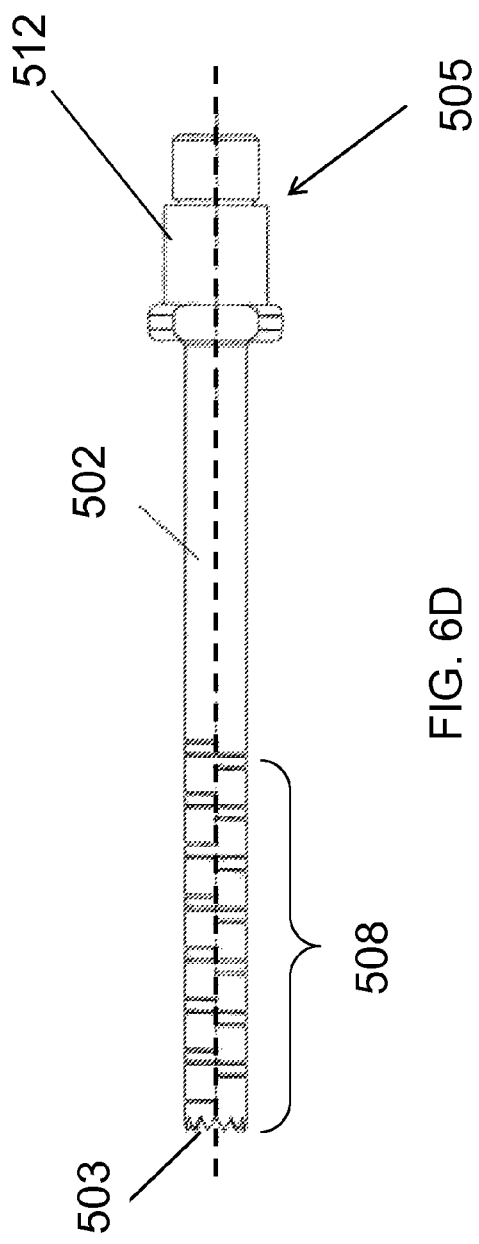
FIG. 6D illustrates a side view of a tube assembly of the stabilizer of FIG. 6A.
Figure 7E:
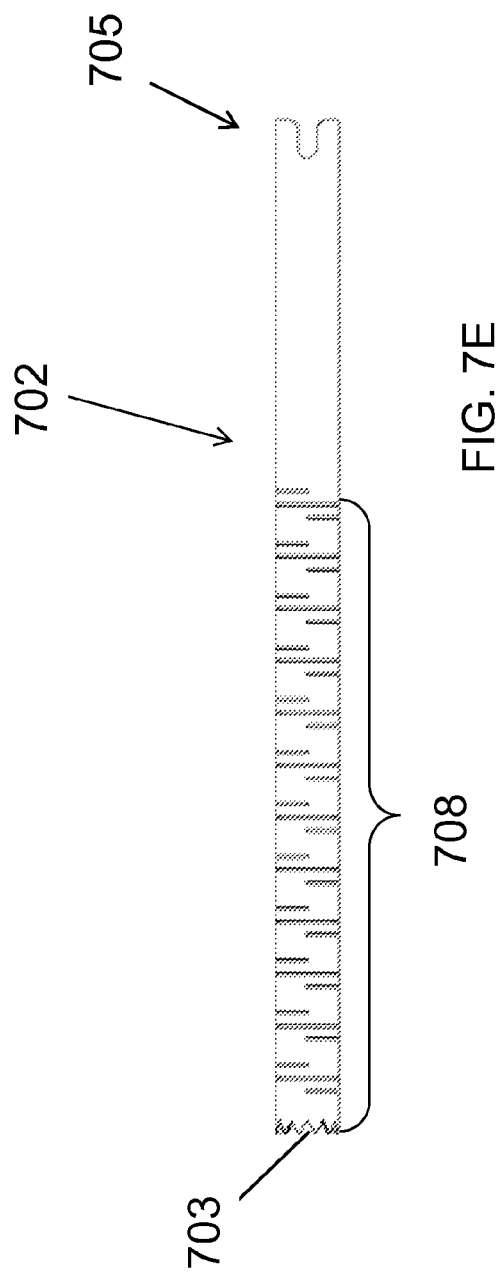
FIG. 7E illustrates a side view of a tube assembly of the stabilizer of FIG. 7A or FIG. 7C.

FIG. 6D illustrates an example of the tube assembly 502 having a distal portion 508, which may be rendered flexible by laser cutting. The tube assembly 502 may be provided with a cutting edge 503, which may be serrated, to score the proximal end of the expandable member 200 to facilitate the subsequent separation of the expandable member 200 from the insertion catheter 101. Proximal end 505 of the tube assembly 502 is configured for insertion into the swivel assembly 510 of the stabilizer 500.

Referring to FIG. 6B and FIG. 6C, the tube assembly 502 may include a swivel assembly 510 disposed at the proximal end 504 for rotating the tube assembly 502. In some embodiments, the swivel assembly 510 may include a swivel coupling 512 rotatably engaged to the tube assembly 512 may be inserted and a knob 514 attached to the swivel coupling 512 by, for example, a set screw 516, for rotating the tube assembly 502.

The stabilizer 500 may further include a handle 516 to allow the user to securely grasp and hold the stabilizer 500 during the separation procedure. The handle 510 may be connected to the tube assembly 502 by the swivel member 512. The handle 510 may be curved or straight as desired based on the procedure.

Referring back to FIG. 5A and FIG. 5B, once the stabilizer 500 is advanced over the insertion catheter 101 to position the distal end 504 of the stabilizer 500 against the proximal end of the expandable portion 200, the user may hold the stabilizer 500 in place by the handle 516 and rotate the tube assembly 502 back and forth using the knob 514 to score the proximal end of the expandable portion 200 with the serrated distal end of the stabilizer 500. In some embodiments, the stabilizer 500 cuts through the material of the expandable portion 200 such that the expandable portion remains attached to the insertion catheter 101 only by a thin film of the hardened light-sensitive liquid.

FIG. 7A, FIG. 7B, FIG. 7C and FIG. 7D illustrate another embodiment of a stabilizer of the present disclosure. Stabilizer 700 is different than stabilizer 500 in that the stabilizer 700 employs a hand-operated clamping collet 710 to enable the stabilizer 700 to securely engage a flexible tube assembly 702. As described above, the flexible tube 702 engaged to the stabilizer 700 can be rotated using a knob 714 to score the insertion catheter 101. The stabilizer 700 may include a handle 716 to facilitate handling of the stabilizer 700. FIG. 7E illustrates an example of the tube assembly 702 having a distal portion 708, which may be rendered flexible by laser cutting. The tube assembly 501 may be provided with a cutting edge 703, which may be serrated, to score the proximal end of the expandable member 200 to facilitate the subsequent separation of the expandable member 200 from the insertion catheter 101. Proximal end 705 of the tube assembly 702 is configured for insertion into the collet 710 of the stabilizer 700. In operation, the stabilizer 700 may be used in a similar manner to the stabilizer 500.

Next, the expandable portion 200 may be separated from the insertion catheter 100. In some embodiments, the insertion catheter 101 is impacted until the remaining bond between the expandable portion 200 and the insertion catheter, such as a layer of the hardened light-sensitive liquid, is broken to free the expandable member 200. An impaction force may be applied to the insertion catheter 101 using any suitable mechanism.

FIG. 8A illustrates an embodiment of a slap hammer 800 that may be used to apply an impaction force on the insertion catheter 101 in order to separate the expandable member 200 from the insertion catheter 101. The slap hammer 800 may include a shaft 802 having a proximal end 804 and a distal end 806. Any suitable mechanism may be used to attach the slap hammer 800 to the insertion catheter 101 and exert a strong clamping force on the insertion catheter 101. A chuck 808 may be disposed at the distal end 806 of the shaft 802 to attach the slap hammer 800 to the insertion catheter 101. For example, as illustrated in FIG. 8B, the chuck 808 may be a split-jaw collet.

Referring back to FIG. 8A, the slap hammer 800 may further include a hammer 810 slidably disposed on the shaft 802. In operation, the hammer 810 may be moved in a proximal direction over the shaft 802 toward a hammer stop 814 to place the hammer 810 into a loaded position. The hammer 810 may then be released to slide over the shaft 802 to a flange 812 to apply an impaction force on the insertion catheter 101 held in the chuck 808 of the slap hammer 800.

Figure 9A:
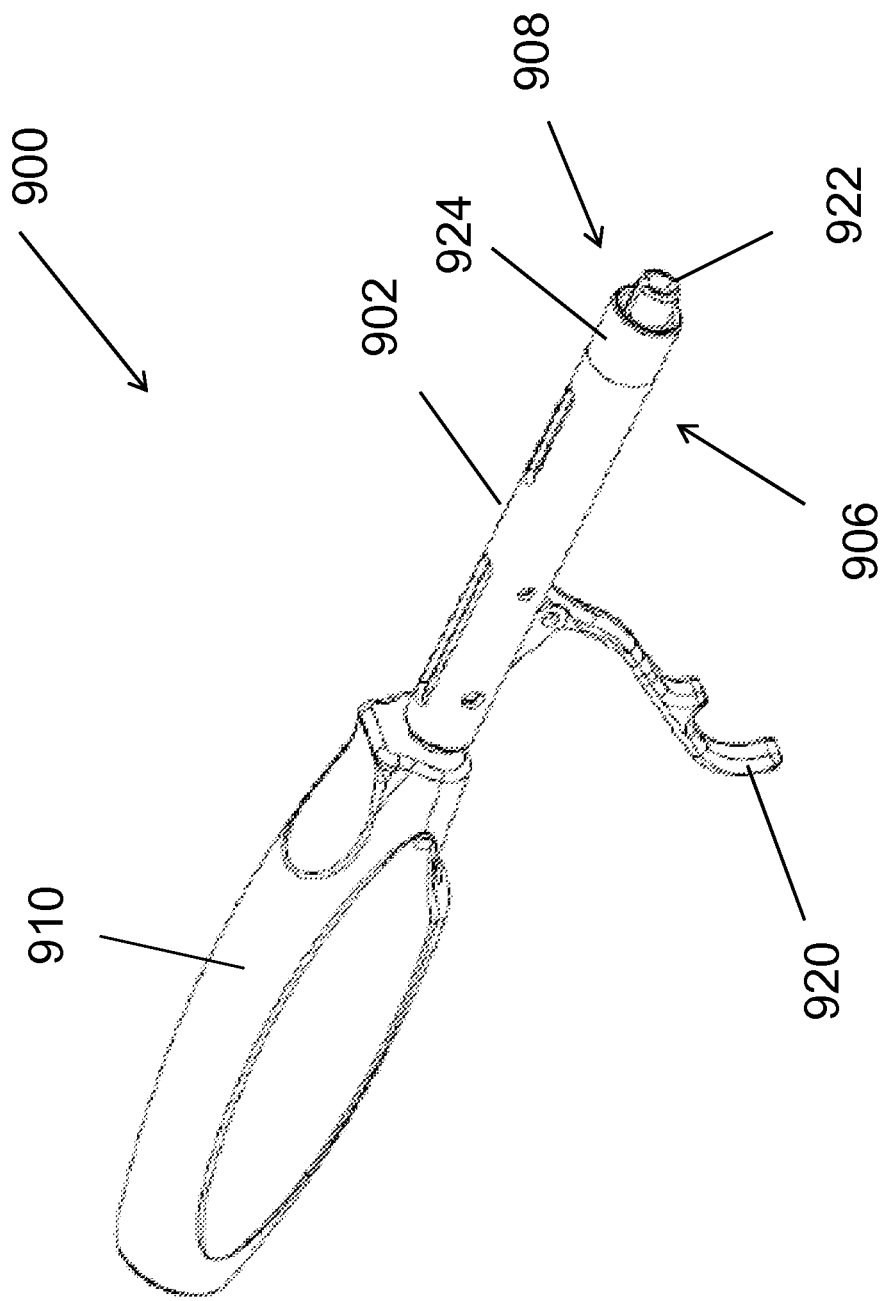
FIG. 9A shows a perspective view of a slap hammer having a trigger and a hammer of the present system.

FIG. 9A illustrates another embodiment of a slap hammer 900 that may be used to apply an impaction force on the insertion catheter 101 in order to separate the expandable member 200 from the insertion catheter 101. The slap hammer 900 includes a shaft 902 having a chuck 908 disposed at the distal end 906 of the shaft 902 to attach the slap hammer 900 to the insertion catheter 101. The chuck 908 includes an outer sleeve 924 and circumferential jaws 922 positioned inside the outer sleeve 924. The slap hammer 900 further includes a trigger mechanism 920 for controlling the jaws 922 of the chuck 908. The slap hammer 900 may further include a hammer 910 slidably disposed on the shaft 902 to apply an impaction force on the insertion catheter 101 held in the chuck 908.

FIG. 9B, FIG. 9C and FIG. 9D illustrate operation of the slap hammer 900. When the trigger 920 is unlocked or open, the outer sleeve 924 is retracted allowing the jaws to open up so the insertion catheter 101 can be inserted into the chuck 908, as shown in FIG. 9B. When the trigger 920 is actuated fully (locked), the outer sleeve 924 is advanced forward over the jaws 922 to force the jaws 922 to clamp down (essentially crimp longitudinally or axially) on the insertion catheter 101, as shown in FIG. 9C. With the trigger 920 fully actuated, the user has a visual feedback that the slap hammer 900 is ready to separate the insertion catheter 101 from the expandable portion 200. In addition to the visual feedback, the user will have some amount of tactile feedback as the resistance (force to pull the trigger 920) of the toggle mechanism is largely overcome about halfway to ¾ of the travel arc. In reference to FIG. 9D, the hammer 910 of the slap hammer 900 may be pulled proximally along the shaft 902 and utilized to apply an impaction force on the insertion catheter 101 held in the chuck 908. When the insertion catheter 101 is separated from the expandable portion 200, the user can release the trigger 920 to open the jaws 922 so the insertion catheter 101 can be removed from the slap hammer 900.

FIG. 10A illustrates another embodiment of a slap hammer, slap hammer 1000, that may be used to apply an impaction force on the insertion catheter 101 in order to separate the expandable member 200 from the insertion catheter 101. The slap hammer 1000 includes a shaft 1002 having internal chamber 1008 with a through-hole 1009 disposed at its distal end 1008 to attach the slap hammer 1000 to the insertion catheter 101. Similar to the slap hammer 900, the slap hammer 1000 includes a trigger 1020 for locking the insertion catheter inside the chamber 1008. The slap hammer 1000 may further include a hammer 1010 slidably disposed on the shaft 1002 to apply an impaction force on the insertion catheter 101 held in the internal chamber 1008.

Referring to FIG. 10B and FIG. 10C, the trigger 1020 includes a projection 1022 on the inner surface 1024 of the trigger 1020 to clamp down on the insertion catheter 101 as the trigger 1020 is being moved from an unlocked or open position, as shown in FIG. 10B, to a locked or closed position, which is shown in FIG. 10C. As the trigger moves into the locked position, the projection 1022 makes a kink in the insertion catheter 101, which provides the clamp or grip on the insertion catheter 101 to prevent axial slip of the insertion catheter 101 as the hammer 1010 of the slap hammer 1000 is actuated. This design also can provide visible, tactile and audible feedback to the user that the trigger 1020 has been actuated fully and correctly. A spring mechanism and lock 1025 may be included to provide an audible "snap" (tactile to some degree as well) when the trigger 1020 is fully and properly deployed. The spring mechanism 1025 may also lock the trigger 1020 in position to prevent the trigger 1020 from opening and inadvertently releasing the insertion catheter 101, during the procedure. With the trigger 1020 locked, the user can then deploy the hammer 1010, slidably disposed on the shaft 1002, to separate the insertion catheter 101 from the expandable portion 200. When the insertion catheter 101 is separated, the user can disengage the spring mechanism 1025 by, for example, depressing a tongue or protrusion 1027 on the spring mechanism 1025, thereby unlocking the trigger 1020 and enabling the trigger 1020 to be disengaged. The trigger 1020 can then be moved to the unlocked position to enable removal of the insertion catheter 101 from the internal chamber 1008.

Referring to FIG. 11, in operation, the slap hammer 800 may be attached to the insertion catheter 101 by inserting the proximal end 112 of the insertion catheter 101 in the chuck 708. The stabilizer 500 may be left in place over the insertion catheter 101. In this manner, the stabilizer 500 provides an opposing force to the impaction force from the slap hammer 800 so that the hardened expandable portion does not migrate in the intramedullary cavity as the expandable portion 200 is being separated from the insertion catheter 101.

As shown in FIG. 12A and FIG. 12B, the chuck 808 is then tightened around the insertion catheter 101 to pinch and compress the insertion catheter 101. In some embodiments, the expandable portion 200 is attached to the inner tube 209 of the insertion catheter 101, as shown in FIG. 2A and FIG. 2B. In such embodiments, the chuck 808 is tightened until the inner tube 209 is pinched to facilitate separation of the expandable portion 200 from the insertion catheter 101.

Next, the user can grasp the stabilizer 500 by the handle 516 and push the stabilizer 500, 700 toward the expandable portion 200 to apply pressure against the proximal end 112 of the expandable portion 200. The slap hammer 800 may then be activated to apply an impaction force on the insertion catheter 101 until the insertion catheter 101 has separated from the expandable portion 200, at which point, the insertion catheter 101 can be withdrawn from the patient, leaving the hardened internal bone fixation device in the bone, as shown, for example, in FIG. 3E. It should be noted that while the methods is described in connection to the stabilizer 500 and the slap hammer 800, the stabilizer 500 can be substituted with the stabilizer 700 and the slap hammer 800 may be substituted with the slap hammers 900 or 1000, and various combinations of the stabilizers and the slap hammers may be employed, to perform methods of the present disclosure.

Portions of the devices disclosed herein are constructed from surgically suitable materials. In some embodiments, portions of the devices are constructed from disposable materials and intended for single-use applications. In some embodiments, portions of the devices are constructed from metal materials. In some embodiments, portions of the devices are constructed from both disposable and metal materials. In some embodiments, portions of the devices are constructed from carbon containing materials. In some embodiments, portions of the devices are constructed from titanium containing materials. In some embodiments, portions of the devices are constructed from aluminum containing materials. In some embodiments, portions of the devices are constructed from a stainless steel material. Examples of stainless steel materials include, but are not limited to, a 300 series stainless steel and a 600 series stainless steel. In some embodiments, portions of the devices disclosed herein are rigid. In some embodiments, portions of the devices disclosed herein are flexible.

In some embodiments, the cutting mechanisms disclosed herein are fabricated as a single component. In some embodiments, the cutting mechanisms disclosed herein are fabricated as multiple components that are welded, adhered, or fastened together. In some embodiments, portions of the devices disclosed herein can be coated with a radiopaque material or can contain radiopaque materials that are known to increase radiopacity, which will allow a person to view the devices using fluoroscopy techniques. In some embodiments, the devices disclosed herein have a diameter ranging from about 2 mm to about 8 mm. In some embodiments, the devices disclosed herein have a diameter ranging from about 3 mm to about 6 mm.

The devices disclosed herein are designed to be small enough to fit within an access hole of a fractured bone.

In some embodiments, a system for separating an internal bone fixation device from an introducer includes a stabilizer configured to score the proximal end of the internal bone fixation device, and a separator configured to engage the introducer and provide an impact to the introducer to separate the introducer from the internal fixation device.

In some embodiments, a method of separating an internal bone fixation device from an introducer includes providing a stabilizer and a separator, wherein the introducer has a shaft attached to the internal bone fixation device, engaging the stabilizer with the proximal end of the introducer; scoring the proximal end of the internal bone fixation device, engaging the separator with the shaft of the introducer, providing an impact on the introducer from the separator to separate the introducer form the internal fixation device using the separator.

In some embodiments, a separation system includes a stabilizer configured to slide over an introducer for delivery of a bone fixation device to a bone cavity, the stabilizer being further configured to score a proximal end of the bone fixation device; and a separator configured to engage the introducer and to provide an impact to the introducer to separate the introducer from the bone fixation device.

In some embodiments, a separation system includes an introducer having a distal end and a proximal end; a bone fixation device engaged to the distal end of the introducer; a stabilizer advanceable over the introducer to a proximal end of the bone fixation device, the stabilizer having a cutting distal edge to score the proximal end of the bone fixation device; and a separator having a shaft attachable to the proximal end of the introducer, and a hammer slidably disposed along the shaft to provide an impaction force on the introducer to separate the introducer from the bone fixation device.

In some embodiments, a method of separating an internal bone fixation device from an introducer includes forming an internal bone fixation device engaged to an introducer in an intramedullary cavity of a bone; scoring a proximal end of the internal bone fixation device; and providing an impact force on the introducer to separate the introducer from the bone fixation device.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims

What is claimed is:

1. A separation system comprising:
   a stabilizer configured to slide over an introducer for delivery of a bone fixation device to a bone cavity, the stabilizer being further configured to score a proximal end of the bone fixation device;
   wherein the stabilizer includes a tube assembly having a cutting distal edge and a swivel assembly engaged to a proximal end of the tube assembly for rotating the tube assembly; and
   a separator configured to engage the introducer and to provide an impact to the introducer to separate the introducer from the bone fixation device.

2. The system of claim 1 wherein the swivel assembly comprises a swivel coupling rotatably engaged to the tube assembly and a knob engaged to the swivel coupling to rotate the tube assembly.

3. The system of claim 1 wherein the swivel assembly comprises a clamping collet into which the tube assembly may be inserted and a knob engaged to the clamping collet for rotating the tube assembly.

4. The system of claim 1 further comprising a handle attached to the swivel assembly of the stabilizer.

5. The system of claim 1 wherein the separator comprises a shaft attachable to the introducer and a hammer slidably disposed on the shaft to provide an impact force on the introducer.

6. The system of claim 5 further comprising a chuck disposed at a distal end of the shaft for receiving the introducer to attach the shaft to the introducer.

7. The system of claim 5 further comprising inner jaws slidably disposed within an outer sleeve and a trigger for moving the outer sleeve between an open position in which the inner jaws are exposed allowing the inner jaws to move apart for receiving the introducer between the inner jaws and a closed position in which the outer sleeve is moved over the inner jaws causing the inner jaws toward one another to engage the introducer to the shaft.

8. The system of claim 5 further comprising a chamber disposed at a distal end of the shaft for receiving the distal end of the introducer and a trigger moveable from an open position in which the trigger is withdrawn from the inner chamber to allow the introducer to be inserted into the inner chamber to a closed position in which the trigger is inserted into the inner chamber to pinch the introducer to secure the introducer within the inner chamber.

9. A separation system comprising:
   an introducer having a distal end and a proximal end;
   a bone fixation device engaged to the distal end of the introducer;
   a stabilizer advanceable over the introducer to a proximal end of the bone fixation device, the stabilizer having a cutting distal edge to score the proximal end of the bone fixation device; and
   a separator having a shaft attachable to the proximal end of the introducer, and a hammer slidably disposed along the shaft to provide an impaction force on the introducer to separate the introducer from the bone fixation device.

10. The system of claim 9 wherein the stabilizer includes a tube assembly having a cutting distal edge and a swivel assembly engaged to a proximal end of the tube assembly for rotating the tube assembly.

11. The system of claim 10 wherein the swivel assembly comprises a swivel coupling rotatably engaged to the tube assembly and a knob engaged to the swivel coupling to rotate the tube assembly.

12. The system of claim 11 wherein the swivel assembly comprises a clamping collet into which the tube assembly may be inserted and a knob engaged to the clamping collet for rotating the tube assembly.

13. The system of claim 11 further comprising a handle attached to the swivel assembly of the stabilizer.

14. The system of claim 9 further comprising a chuck disposed at a distal end of the shaft for receiving the introducer to attach the shaft to the introducer.

15. The system of claim 9 further comprising inner jaws slidably disposed within an outer sleeve and a trigger for moving the outer sleeve between an open position in which the inner jaws are exposed allowing the inner jaws to move apart for receiving the introducer between the inner jaws and a closed position in which the outer sleeve is moved over the inner jaws causing the inner jaws toward one another to engage the introducer to the shaft.

16. The system of claim 9 further comprising a chamber disposed at a distal end of the shaft for receiving the distal end of the introducer and a trigger moveable from an open position in which the trigger is withdrawn from the inner chamber to allow the introducer to be inserted into the inner chamber to a closed position in which the trigger is inserted into the inner chamber to pinch the introducer to secure the introducer within the inner chamber.

17. A method of separating an internal bone fixation device from an introducer, the method comprising:
   forming an internal bone fixation device engaged to an introducer in an intramedullary cavity of a bone;
   scoring a proximal end of the internal bone fixation device; and
   providing an impact force on the introducer to separate the introducer from the bone fixation device.

18. The method of claim 17 wherein the bone fixation device is formed by filling an expandable portion of the introducer with a light-sensitive liquid and exposing the light-sensitive liquid within the expandable portion to light to cure the light-sensitive liquid.

19. The method of claim 18 wherein the light is delivered into the expandable member from an outside light source by a light-conducting fiber passed though the introducer.

20. A separation system comprising:
   a stabilizer configured to slide over an introducer for delivery of a bone fixation device to a bone cavity, the stabilizer being further configured to score a proximal end of the bone fixation device; and
   a separator configured to engage the introducer and to provide an impact to the introducer to separate the introducer from the bone fixation device;
   wherein the separator comprises a shaft attachable to the introducer and a hammer slidably disposed on the shaft to provide an impact force on the introducer.

21. The system of claim 20 further comprising a chuck disposed at a distal end of the shaft for receiving the introducer to attach the shaft to the introducer.

22. The system of claim 20 further comprising inner jaws slidably disposed within an outer sleeve and a trigger for moving the outer sleeve between an open position in which the inner jaws are exposed allowing the inner jaws to move apart for receiving the introducer between the inner jaws and a closed position in which the outer sleeve is moved over the inner jaws causing the inner jaws toward one another to engage the introducer to the shaft.

23. The system of claim 20 further comprising a chamber disposed at a distal end of the shaft for receiving the distal end of the introducer and a trigger moveable from an open position in which the trigger is withdrawn from the inner chamber to allow the introducer to be inserted into the inner chamber to a closed position in which the trigger is inserted into the inner chamber to pinch the introducer to secure the introducer within the inner chamber.

\* \* \* \* \*

UNITED STATES PATENT AND TRADEMARK OFFICE
CERTIFICATE OF CORRECTION

PATENT NO. : 8,939,977 B2  
APPLICATION NO. : 13/800518  
DATED : January 27, 2015  
INVENTOR(S) : Gene P. DiPoto et al.

Page 1 of 1

It is certified that error appears in the above-identified patent and that said Letters Patent is hereby corrected as shown below:

In the claims:

Column 18, Claims 12 and 13 replace "The system of claim 11" with --The system of claim 10--.

Signed and Sealed this  
Eighth Day of March, 2016

Michelle K. Lee  
*Director of the United States Patent and Trademark Office*